(12) United States Patent
Langston et al.

(10) Patent No.: US 10,072,029 B2
(45) Date of Patent: Sep. 11, 2018

(54) CRYSTALLINE FORM OF A PROTEASOME INHIBITOR

(71) Applicant: Millennium Pharmaceuticals, Inc., Cambridge, MA (US)

(72) Inventors: Marianne Langston, North Andover, MA (US); Debra Mazaik, Holliston, MA (US); Eric Elliott, Watertown, MA (US); Anton Peterson, Holliston, MA (US); Patricia Andres, West Lafayette, IN (US); Jing Teng, West Lafayette, IN (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 15/550,132

(22) PCT Filed: Feb. 10, 2016

(86) PCT No.: PCT/US2016/017420
§ 371 (c)(1),
(2) Date: Aug. 10, 2017

(87) PCT Pub. No.: WO2016/130724
PCT Pub. Date: Aug. 18, 2016

(65) Prior Publication Data
US 2018/0044356 A1    Feb. 15, 2018

Related U.S. Application Data

(60) Provisional application No. 62/114,838, filed on Feb. 11, 2015, provisional application No. 62/265,762, filed on Dec. 10, 2015.

(51) Int. Cl.
*C07F 5/05* (2006.01)
*A61K 31/573* (2006.01)
*A61K 31/454* (2006.01)
*A61K 31/675* (2006.01)
*A61K 31/197* (2006.01)
*A61K 31/69* (2006.01)

(52) U.S. Cl.
CPC ............. *C07F 5/05* (2013.01); *A61K 31/197* (2013.01); *A61K 31/454* (2013.01); *A61K 31/573* (2013.01); *A61K 31/675* (2013.01); *A61K 31/69* (2013.01); *C07B 2200/13* (2013.01)

(58) Field of Classification Search
None
See application file for complete search history.

(56) References Cited

U.S. PATENT DOCUMENTS

2009/0325903 A1* 12/2009 Elliott ................... C07F 5/025
514/64

* cited by examiner

*Primary Examiner* — Kamal Saeed
(74) *Attorney, Agent, or Firm* — Honigman Miller Schwartz and Cohn LLP; Lucy X. Yang; Jonathan P. O'Brien

(57) ABSTRACT

The present disclosure relates to a novel crystalline form of a proteasome inhibitor, and to the processes for the preparation thereof. The novel crystalline form according to the disclosure may be used in the preparation of pharmaceutical compositions for the treatment of cancer.

23 Claims, 11 Drawing Sheets

|  | Crystalline Pattern B |
|---|---|
| Bravais Type | Primitive Monoclinic |
| a [Å] | 15.521 |
| b [Å] | 11.032 |
| c [Å] | 15.917 |
| α [deg] | 90 |
| β [deg] | 107.06 |
| γ [deg] | 90 |
| Volume [Å³/cell] | 2,605.5 |
| Chiral Contents? | Chiral |
| Extinction Symbol | P 1 2$_1$ 1 |
| Space Group(s) | P2$_1$ (4) |

CRYSTALLINE FORM OF A PROTEASOME INHIBITOR

CROSS-REFERENCE TO RELATED APPLICATIONS

This application is a 35 U.S.C. § 371 United States National Phase Application of, and claims priority to, PCT Application No.: PCT/US2016/017420 filed Feb. 10, 2016, which claims the benefit under 35 U.S.C. § 119 of U.S. Application Ser. No. 62/114,838, filed Feb. 11, 2015, and U.S. application Ser. No. 62/265,762, filed Dec. 10, 2015. The entire contents of the aforesaid applications are incorporated by reference herein in its entirety.

FIELD

The present disclosure relates to a novel crystalline form of a proteasome inhibitor, and to the processes for the preparation thereof. The novel crystalline form according to the disclosure may be used in the preparation of pharmaceutical compositions for the treatment of cancer.

BACKGROUND

Boronic acid and its derivatives display a variety of pharmaceutically useful biological activities. Shenvi et al., U.S. Pat. No. 4,499,082 (1985) discloses that peptide boronic acids are inhibitors of certain proteolytic enzymes. Kettner and Shenvi, U.S. Pat. No. 5,187,157 (1993), U.S. Pat. No. 5,242,904 (1993), and U.S. Pat. No. 5,250,720 (1993), describe a class of peptide boronic acids that inhibit trypsin-like proteases. Kleeman et al., U.S. Pat. No. 5,169,841 (1992), discloses N-terminally modified peptide boronic acids that inhibit the action of renin. Kinder et al., U.S. Pat. No. 5,106,948 (1992), discloses that certain boronic acid compounds inhibit the growth of cancer cells. Bachovchin et al., WO 07/0005991, discloses peptide boronic acid compounds that inhibit fibroblast activating protein.

Boronic acid and ester compounds hold particular promise as inhibitors of the proteasome, a multicatalytic protease responsible for the majority of intracellular protein turnover. Adams et al., U.S. Pat. No. 5,780,454 (1998), describes peptide boronic ester and acid compounds useful as proteasome inhibitors. The reference also describes the use of boronic ester and acid compounds to reduce the rate of muscle protein degradation, to reduce the activity of NF-κB in a cell, to reduce the rate of degradation of p53 protein in a cell, to inhibit cyclin degradation in a cell, to inhibit the growth of a cancer cell, and to inhibit NF-κB dependent cell adhesion. Furet et al., WO 02/096933, Chatterjee et al., WO 05/016859, and Bernadini et al, WO 05/021558 and WO 06/08660, disclose additional boronic ester and acid compounds that are reported to have proteasome inhibitory activity.

[(1R)-1-({[(2,5-dichlorobenzoyl)amino]acetyl}amino)-3-methylbutyl]boronic acid, also known as ixazomib, is a proteasome inhibitor in the peptide boronic acid class. Ixazomib selectively inhibits the proteasome. Ixazomib preferentially binds the β5 site of the 20S proteasome with a concentration producing 50% inhibition (IC50) of 3.4 nM. At higher concentrations, it also inhibits the activity of the β1 and β2 sites. Ixazomib is selective for the proteasome when tested against a panel of proteases ($IC_{50}$ values between 20 and 100 µM), kinases ($IC_{50}$ values>10 µM), and receptors ($IC_{50}$ values>10 µM). Ixazomib citrate has been evaluated at clinical studies that have included patients with advanced solid tumors, lymphoma, relapsed/refractory multiple myeloma (RRMM), and amyloidosis or relapsed or refractory light-chain (AL) amyloidosis and demonstrated signs of activity. Ongoing studies continue to investigate both single-agent ixazomib citrate and ixazomib citrate in combination with standard treatments. Additional clinic studies are evaluating ixazomib citrate in combination with lenalidomide and dexamethasone (LenDex) versus placebo/LenDex.

Under dehydrating conditions, [(1R)-1-({[(2,5-dichlorobenzoyl)amino]acetyl}amino)-3-methylbutyl]boronic acid readily forms anhydrides by combination of two or more molecules of a boronic acid compound, with loss of one or more water molecules. When mixed with water, the boronic acid anhydrides are hydrated to release the free boronic acid compounds. Boronic acids and their derivatives are often air-sensitive. For example, Korcek et al., *J. Chem. Soc., Perkin Trans.* 2 242 (1972), teaches that butylboronic acid is readily oxidized by air to generate 1-butanol and boric acid.

The manufacturing of a pharmaceutical composition poses many challenges to the chemist and chemical engineer. While many of these challenges relate to the handling of large quantities of reagents and control of large-scale reactions, the handling of the final product poses special challenges linked to the nature of the final active product itself. Not only should the product be prepared in high yield, be stable, and be capable of ready isolation, the product should possess properties that are suitable for the types of pharmaceutical preparations in which they are likely to be ultimately used. The stability of the active ingredient of the pharmaceutical preparation must be considered during each step of the manufacturing process, including the synthesis, isolation, bulk storage, pharmaceutical formulation and long-term storage. Each of these steps may be impacted by various environmental conditions of temperature and humidity.

A primary concern for the manufacture of pharmaceutical compounds is that the active substance should have a stable crystalline morphology to ensure consistent processing parameters and pharmaceutical quality. If an unstable crystalline form is used, crystal morphology may change during manufacture and/or storage resulting in quality control problems and formulation irregularities. Such a change may affect the reproducibility of the manufacturing process and thus lead to final formulations which do not meet the high quality and stringent requirements imposed on formulations of pharmaceutical compositions. There is thus a continuing need for an additional stable form of [(1R)-1-({[(2,5-dichlorobenzoyl)amino]acetyl}amino)-3-methylbutyl]boronic acid or anhydrides thereof.

DESCRIPTION

Figure 1:
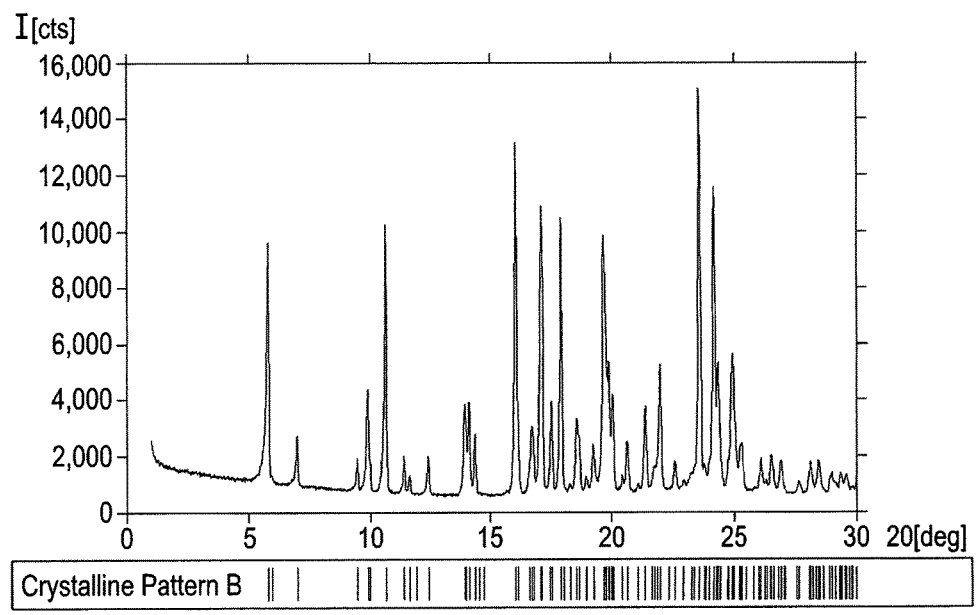
FIG. 1 shows an indexing solution an X-ray powder diffraction pattern (XRPD) of crystalline Pattern B.

Unless otherwise stated, structures depicted herein are meant to include compounds which differ only in the presence of one or more isotopically enriched atoms. For example, compounds having the present structure except for the replacement of a hydrogen atom by a deuterium or tritium, or the replacement of a carbon atom by a $^{13}$C- or $^{14}$C-enriched carbon are within the scope of the present disclosure.

As used herein, "crystalline" refers to a solid in which the constituent atoms, molecules, or ions are packed in a regularly ordered, repeating three-dimensional pattern having a highly regular chemical structure. In particular, a crystalline compound or salt might be produced as one or more crystalline forms. For the purposes of this application, the terms "crystalline form" and "polymorph" are synonymous; the terms distinguish between crystals that have different properties (e.g., different XRPD patterns, different DSC scan results). Pseudopolymorphs are typically different solvates of a material, and thus the properties of pseudopolymorphs differ from one another.

Some embodiments of the disclosure are directed to compounds wherein at least a particular percentage by weight of the compound is crystalline. Some embodiments of the invention are directed to a compound wherein at least a particular percentage by weight of the compound is crystalline. Particular weight percentages include 10%, 20%, 30%, 40%, 50%, 60%, 70%, 75%, 80%, 85%, 87%, 88%, 89%, 90%, 91%, 92%, 93%, 94%, 95%, 96%, 97%, 98%, 99%, 99.5% and 99.9%, When a particular percentage by weight of the compound is crystalline, the remainder of the compound is the amorphous form of the compound. When a particular percentage by weight of the compound is a designated crystalline form, the remainder of the compound is some combination of the amorphous form of the compound, and one or more crystalline forms of the compound excluding the designated crystalline form.

When a crystalline form of a compound is identified using one or more XRPD peaks given as angles 2θ, each of the 2θ values is understood to mean the given value±0.2 degrees, unless otherwise expressed, for example as the given value±0.3.

When a crystalline form of a compound is identified using one or more temperatures from a DSC profile (e.g., onset of endothermic transition, melt, etc.), each of the temperature values is understood to mean the given value±2° C., unless otherwise expressed.

The term "hydrate" refers to a solvate wherein the solvent molecule is H$_2$O that is present in a defined stoichiometric amount, and includes, for example, hemi hydrates, monohydrates, dihydrates, and trihydrates.

The term "seeding" refers to the addition of crystalline material to a solution or mixture to initiate crystallization.

In some embodiments, the present disclosure provides a crystalline form comprising N,N',N''-[2,4,6-boroxintriyltris[[(1R)-3-methylbutylidene]imino(2-oxo-2,1-ethanediyl)]]tris(2,5-dichlorobenzamide).

In some embodiments, the present disclosure provides crystalline Pattern B comprising N,N',N''-[2,4,6-boroxintriyltris[[(1R)-3-methylbutylidene]imino(2-oxo-2,1-ethanediyl)]]tris(2,5-dichlorobenzamide).

In some embodiments, the present disclosure further provides methods for the preparation of the crystalline Pattern B and pharmaceutical compositions comprising crystalline Pattern B, and a pharmaceutically acceptable carrier.

In some embodiments, the present disclosure further provides a method of treating cancer, comprising administering to a patient in need thereof crystalline Pattern B, wherein the cancer includes multiple myeloma, refractory or recurrence multiple myeloma, or lymphoma. In some embodiments, the present disclosure further provides a method of treating amyloidosis, comprising administering to a patient in need thereof crystalline Pattern B. A use of crystalline Pattern B in treating cancer in a patient in need thereof is also provided. A use of crystalline Pattern B in the manufacture of a medicament for treating cancer is also provided.

[(1R)-1-({[(2,5-dichlorobenzoyl)amino]acetyl}amino)-3-methylbutyl]boronic acid has the following Formula (Ia):

Formula (Ia)

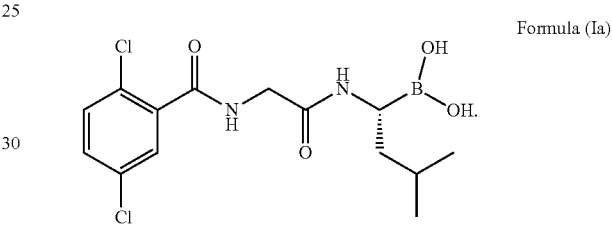

Under dehydrating conditions, this compound forms anhydrides by combination of two or more molecules, with loss of one or more water molecules. In various embodiments, the boronic acid anhydride can comprise two, three, four, or more boronic acid units, and can have a cyclic or linear configuration. In some embodiments, [(1R)-1-({[(2,5-dichlorobenzoyl)amino]-acetyl}amino)-3-methylbutyl]boronic acid form a cyclic trimer (boroxine). In one embodiment, a cyclic trimer is N,N',N''-[2,4,6-boroxintriyltris[[(1R)-3-methylbutylidene]imino(2-oxo-2,1-ethanediyl)]]tris(2,5-dichlorobenzamide) of Formula (Ib):

Formula (Ib)

Chemical synthesis of Formula (Ia) or Formula (Ib) are described in WO 2009/02448, U.S. Pat. No. 7,442,830, WO 2009/154737 and U.S. Pat. No. 8,859,504, which are incorporated herein by reference in their entirety.

In some embodiments, the compound of Formula (Ib) may be depicted in one or more alternate resonance forms. A resonance form is another way of drawing a Lewis dot structure for a given compound. Equivalent Lewis structures are called resonance forms. They are used when there is more than one way to place double bonds and lone pairs on atoms. For example, the compound of Formula (Ib) may be alternatively depicted as Formula (Ic) or Formula (Id) below:

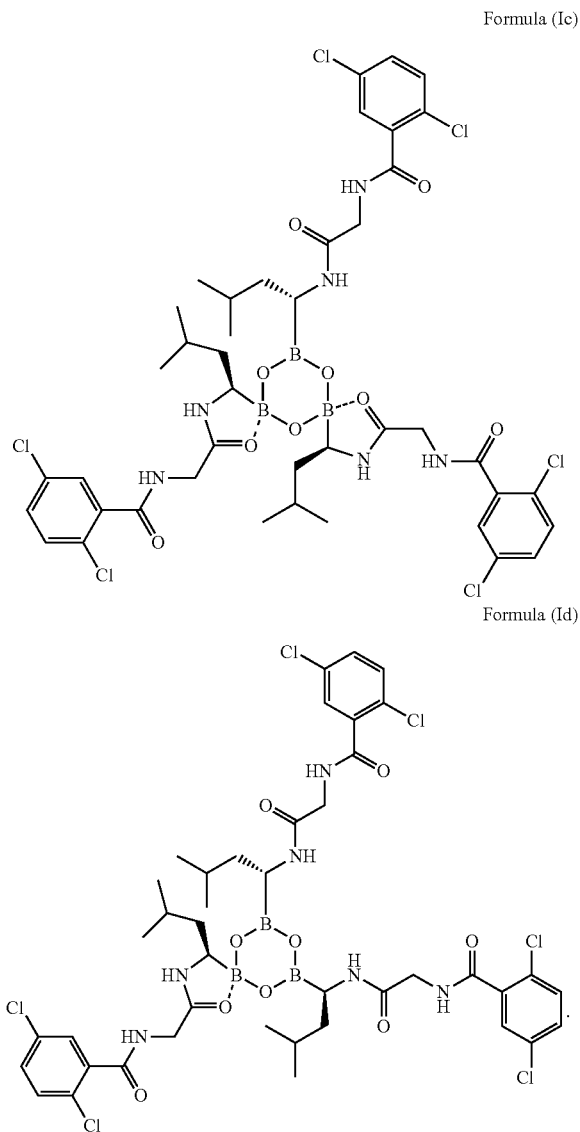

Formula (Ic)

Formula (Id)

Provided herein is an assortment of characterizing information, which is sufficient, but not ab of which is necessary, to describe crystalline Pattern B. Crystalline Pattern B has properties that make it suitable for large-scale pharmaceutical formulation manufacture, such as stability.

In some embodiments, crystalline Pattern B of this disclosure has an X-ray powder diffraction pattern having characteristic peaks expressed in degrees two-theta at approximately 5.79±0.20, 10.63±0.20, 16.06±0.20, and 23.58±0.20.

In some embodiments, crystalline Pattern B of this disclosure has an X-ray powder diffraction pattern having characteristic peaks expressed in degrees two-theta at approximately 5.79±0.20, 10.63±0.20, 16.06±0.20, 17.12±0.20, 17.93±0.20, 19.69±0.20, 23.58±0.20, and 24.17±0.20.

In some embodiments, crystalline Pattern B of this disclosure has an X-ray powder diffraction pattern having characteristic peaks expressed in degrees two-theta at approximately 5.79±0.20, 10.63±0.20, 16.06±0.20, 17.12±0.20, 17.93±0.20, 19.69±0.20, 23.58±0.20, 24.17±0.20 and 24.93±0.20.

In some embodiments, crystalline Pattern B is characterized by an XRPD pattern having a reference peak expressed in degrees two-theta at 5.79±0.20, and having peaks expressed in degrees two-theta at 4.84, 10.27, 17.79 relative to the reference peak. The term "reference peak" refers to a peak in the XRPD diffractogram that one skilled in the art considers as informing the polymorphic form of the material, i.e., differentiated from instrument noise. By "relative" it is meant that the observed two-theta angle of each peak will be the sum of the two-theta angle of the reference peak and the relative two-theta angle of that peak. For example, if the reference peak has a two-theta angle in degrees of 5.69, the relative peaks will have two-theta angles in degrees of 4.94, 10.37, 17.89; if the reference peak has a two-theta angle in degrees of 5.79, the relative peaks will have two-theta angles in degrees of 4.84, 10.27, 17.79; if the reference peak has a two-theta angle in degrees of 5.89, the relative peaks will have two-theta angles in degrees of 4.74, 10.17, 17.69; etc. In some embodiments, crystalline Pattern B is characterized by an XRPD pattern having a reference peak expressed in degrees two-theta at 5.79±0.20, and having peaks expressed in degrees two-theta at 4.84, 10.27, 11.33, 12.14, 13.90, 17.79, 18.38, relative to the reference peak. In some embodiments, crystalline Pattern B is characterized by an XRPD pattern having a reference peak expressed in degrees two-theta at 5.79±0.20, and having peaks expressed in degrees two-theta at 4.84, 10.27, 11.33, 12.14, 13.90, 17.79, 18.38, 19.14 relative to the reference peak. Any of the peaks that one skilled in the art considers as informing the polymorphic form of the material can serve as the reference peak and the relative peaks can then be calculated. For example, if the reference peak has a two-theta angle in degrees of 23.58, then the relative peaks will have two-theta angles in degrees of −17.79, −12.95, and −7.52 relative to the reference peak.

In one embodiment, crystalline Pattern B comprises at least 98.0% of the compound of Formula (Ib).

In another embodiment, crystalline Pattern B comprises at least 98.5% of the compound of Formula (Ib).

In another embodiment, crystalline Pattern B comprises at least 99.0% of the compound of Formula (Ib).

In another embodiment, crystalline Pattern B comprises at least 99.5% of the compound of Formula (Ib).

In another embodiment, crystalline Pattern B comprises at least 99.8% of the compound of Formula (Ib).

In another embodiment, crystalline Pattern B comprises at least 99.9% of the compound of Formula (Ib).

In another embodiment, crystalline Pattern B comprises 100% of the compound of Formula (Ib).

In some embodiments, crystalline Pattern B is prepared using a method (Method A) comprising the steps of:
 (a) adding a non-crystalline solid comprising a compound of Formula (Ib) to a solvent or solvent mixture;

(b) stirring the resulting mixture for a sufficient amount of time at a predetermined temperature to form crystalline Pattern B; and optionally
(c) isolating crystalline Pattern B.

In some embodiments, the resulting mixture is a slurry. In some embodiments the resulting mixture is a solution.

In some embodiments, the non-crystalline solid in the method may include a small amount of the boronic acid of Formula (Ia). For example, the non-crystalline solid may include 10%, 5%, 2%, 1%, 0.5%, 0.3%, 0.2%. 0.1, or 0.01% of the boronic acid of Formula (Ia).

In some embodiments, the non-crystalline solid in the method comprises at least 80%, 90%, 95%, 98%, 99%, 99.50%, 99.80%, 99.90 or 99.99% of the cyclic trimer of Formula (Ib). In some embodiments, the non-crystalline solid comprises 100% of the cyclic trimer of Formula (Ib).

In some embodiments, the solvent or solvent mixture is acetone/water (1:3), DMF/water (1:2), isopropyl acetate, or THF/water (1:10). The solvent mixtures are prepared in terms of volume to volume ratios.

In some embodiments, the predetermined temperature is about 15° C. to about 35° C. In other embodiments, the temperature is about 15° C., 20° C., 25° C., 30° C., or 35° C.

In some embodiments, the predetermined temperature is room temperature. In some embodiments, room temperature is about 15° C. to about 35° C.

In some embodiments, room temperature is about 15° C., 20° C., 25° C., 30° C., or 35° C.

In some embodiments, the isolation may be achieved by filtration, optionally followed by drying under reduced pressure.

In some embodiments, step (b) further comprises adding crystalline Pattern B as seeding material to the resulting mixture. In such embodiments, the solvent or solvent mixture is THF/ACN (1:5), THF/diisopropyl ether (1:5), THF/toluene (1:5). The solvent mixtures are prepared in terms of volume to volume ratios.

In some embodiments, the sufficient amount of time to form crystalline Pattern B is about 1 to about 10 days. In other embodiments, the sufficient amount of time is about 2 to about 5 days.

In some embodiments, crystalline Pattern B is prepared using a method (Method B) comprising the steps of:
(a) dissolving or suspending a non-crystalline solid comprising a compound of Formula (Ib) in a solvent;
(b) adding a second agent to the suspension or solution at a predetermined temperature;
(c) stirring the above mixture for a sufficient amount of time to form crystalline Pattern B; and optionally
(d) isolating crystalline Pattern B.

In some embodiments, the non-crystalline solid in the method may include a small amount of the boronic acid of Formula (Ia). For example, the non-crystalline solid may include 10%, 5%, 2%, 1%, 0.5%, 0.3%, 0.2%. 0.1, or 0.01% of the boronic acid of Formula (Ia).

In some embodiments, the non-crystalline solid in the method comprises at least 80%, 90%, 95%, 98%, 99%, 99.50%, 99.80%, 99.90 or 99.99% of the cyclic trimer of Formula (Ib). In some embodiments, the non-crystalline solid comprises 100% of the cyclic trimer of Formula (Ib).

In some embodiments, the solvent is ethyl acetate.

In some embodiments, the second agent is anethole, methyl benzoate, methyl cinnamate, triacetin, triethyl citrate, or caffeine. In some embodiments, the second agent is methyl cinnamate.

In some embodiments, the isolated crystalline Pattern B may contain the second agent. In some embodiments, the amount of the second agent in the isolated crystalline Pattern B is about 0.1%, 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, 10.5%, 11%, 11.5%, 12%, 12.5%, 13%, 13.5%, 14%, 14.5%, 15%, 15.5%, 16%, 16.5%, 17%, 17.5%, 18%, 18.5%, 19%, 19.5%, or 20% by weight of the crystalline Pattern B. In some embodiments, the amount of the second agent in the isolated crystalline Pattern B is between 0% and 5% by weight of the crystalline Pattern B. In some embodiments, the amount of the second agent in the isolated crystalline Pattern B is between 0% and 10% by weight of the crystalline Pattern B. In some embodiments, the amount of the second agent in the isolated crystalline Pattern B is about 4.5% by weight of the crystalline Pattern B.

In some embodiments, the predetermined temperature is about 15° C. to about 35° C. In other embodiments, the temperature is about 15° C., 20° C., 25° C., 30° C., or 35° C.

In some embodiments, the predetermined temperature is room temperature, from about 15° C. to about 35° C.

In some embodiments, room temperature is about 15° C., 20° C., 25° C., 30° C., or 35° C.

In some embodiments, the isolation may be achieved by filtration, optionally followed by drying under reduced pressure.

In some embodiments, the sufficient amount of time to generate crystalline Pattern B is about 4 hours to 24 hours. In other embodiments, the sufficient amount of time is about 6, 8, 10, 12, 14, or 16 hours.

In some embodiments, the present disclosure provides a process for producing large amounts of crystalline Pattern B. The process comprises the steps of:
(a) adding crystalline Pattern B as seeding material to a solution of non-crystalline solid comprising the compound of Formula (Ib);
(b) stirring the solution at a predetermined temperature for a sufficient amount of time; and optionally
(c) collecting crystalline Pattern B.

In some embodiments, the non-crystalline solid in the process may include a small amount of the boronic acid of Formula (Ia). For example, the non-crystalline solid may include 10%, 5%, 2%, 1%, 0.5%, 0.2%. 0.1, or 0.01% of the boronic acid of Formula (Ia).

In some embodiments, the non-crystalline solid in the process comprises at least 90%, 95%, 98%, 99%, 99.50%, 99.80%, 99.90 or 99.99% of the cyclic trimer of formula (Ib). In some embodiments, the non-crystalline solid comprises 100% of the cyclic trimer of formula (Ib).

In some embodiments, the solution is ethyl acetate solution.

In some embodiments, the amount of crystalline Pattern B as seeding material in the process is about from 0.1% to about 5% by weight of the non-crystalline solid. In some embodiments, the amount of crystalline Pattern B as seeding material is from about 5% to about 10% by weight of the non-crystalline solid. In some embodiments, the amount of crystalline Pattern B as seeding material is about from 10% to about 20% by weight of the non-crystalline solid. In some embodiments, the amount of crystalline Pattern B as seeding material is about 0.1%, 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, 10.5%, 11%, 11.5%, 12%, 12.5%, 13%, 13.5%, 14%, 14.5%, 15%, 15.5%, 16%, 16.5%, 17%, 17.5%, 18%, 18.5%, 19%, 19.5%, or 20% by weight of the non-crystalline solid.

In some embodiments, the crystalline Pattern B used as seeding material is generated by the Method B above. In some embodiments, the crystalline Pattern B used as seeding material may include small amounts of the second agent. In some embodiments, the second agent is anethole, methyl benzoate, methyl cinnamate, triacetin, triethyl citrate, or caffeine. In some embodiments, the crystalline Pattern B used as seeding material includes small amounts of methyl cinnamate. In some embodiments, the amount of the second agent in the crystalline Pattern B used as seeding material is about 0.1%, 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, 10.5%, 11%, 11.5%, 12%, 12.5%, 13%, 13.5%, 14%, 14.5%, 15%, 15.5%, 16%, 16.5%, 17%, 17.5%, 18%, 18.5%, 19%, 19.5%, or 20% by weight of the crystalline Pattern B. In some embodiments, the amount of the second agent in the crystalline Pattern B used as seeding material is between 0 and 5% by weight of the crystalline Pattern B. In some embodiments, the amount of the second agent in the crystalline Pattern B used as seeding material is between 0 and 10% by weight of the crystalline Pattern B. In some embodiments, the amount of the second agent in the crystalline Pattern B used as seeding material is about is about 4.5% by weight of the crystalline Pattern B.

In some embodiments, the temperature in the process is between about 15° C. to about 40° C. In other embodiments, the temperature is about 15° C., 20° C., 25° C., 30° C., or 35° C.

In some embodiments, the predetermined temperature is room temperature, from about 15° C. to about 35° C.

In some embodiments, room temperature is about 15° C., 20° C., 25° C., 30° C., or 35° C.

In some embodiments, the collecting step of the process may be achieved by filtration, optionally followed by drying under reduced pressure.

In some embodiments, the sufficient amount of time for the process is from 4 hours to 24 hours. In other embodiments, the sufficient amount of time is about 6, 8, 10, 12, 14, or 16 hours.

In one embodiment, crystalline Pattern B can be characterized as having an X-ray diffraction pattern having characteristic peaks (2θ) as shown in Table 1. A discussion of the theory of X-ray powder diffraction patterns can be found in Stout & Jensen, *X-Ray Structure Determination; A Practical Guide*, MacMillan Co., New York, N.Y. (1968), which is incorporated by reference in its entirety. The X-ray Powder Diffraction (XRPD) patterns were acquired using Cu-Kα radiation. Unless stated otherwise, all XRPD values described herein are measured on a 2-Theta (2θ) scale.

TABLE 1

List of XRPD Peaks (±0.2 degrees)

| Angles (°2θ) | Intensity (%) |
|---|---|
| 5.79 | 100 |
| 6.98 | 18 |
| 9.46 | 13 |
| 9.89 | 33 |
| 10.63 | 70 |
| 11.40 | 16 |
| 12.41 | 13 |
| 13.96 | 32 |
| 14.13 | 29 |
| 14.38 | 16 |
| 16.06 | 75 |
| 16.73 | 27 |
| 17.12 | 68 |

TABLE 1-continued

List of XRPD Peaks (±0.2 degrees)

| Angles (°2θ) | Intensity (%) |
|---|---|
| 17.53 | 23 |
| 17.93 | 61 |
| 18.58 | 28 |
| 19.26 | 20 |
| 19.69 | 68 |
| 20.05 | 25 |
| 20.65 | 18 |
| 21.37 | 24 |
| 21.99 | 33 |
| 22.59 | 11 |
| 23.58 | 80 |
| 24.17 | 67 |
| 24.33 | 32 |
| 24.93 | 39 |
| 25.26 | 15 |
| 26.11 | 12 |
| 26.54 | 13 |
| 26.92 | 11 |
| 28.12 | 11 |
| 28.46 | 11 |
| 29.36 | 11 |
| 29.59 | 10 |

In one embodiment, the indexing solution from the XRPD pattern for crystalline Pattern B exhibits a primitive monoclinic unit cell having chiral contents, a P2$_1$ (4) space group, a volume of 2,605.5 Å$^3$, the extinction symbol P 1 2$_1$ 1, and the following dimensions:

| | |
|---|---|
| a | 15.521 Å |
| b | 11.032 Å |
| c | 15.917 Å |
| α | 90° |
| β | 107.06° |
| γ | 90° |

Figure 7:
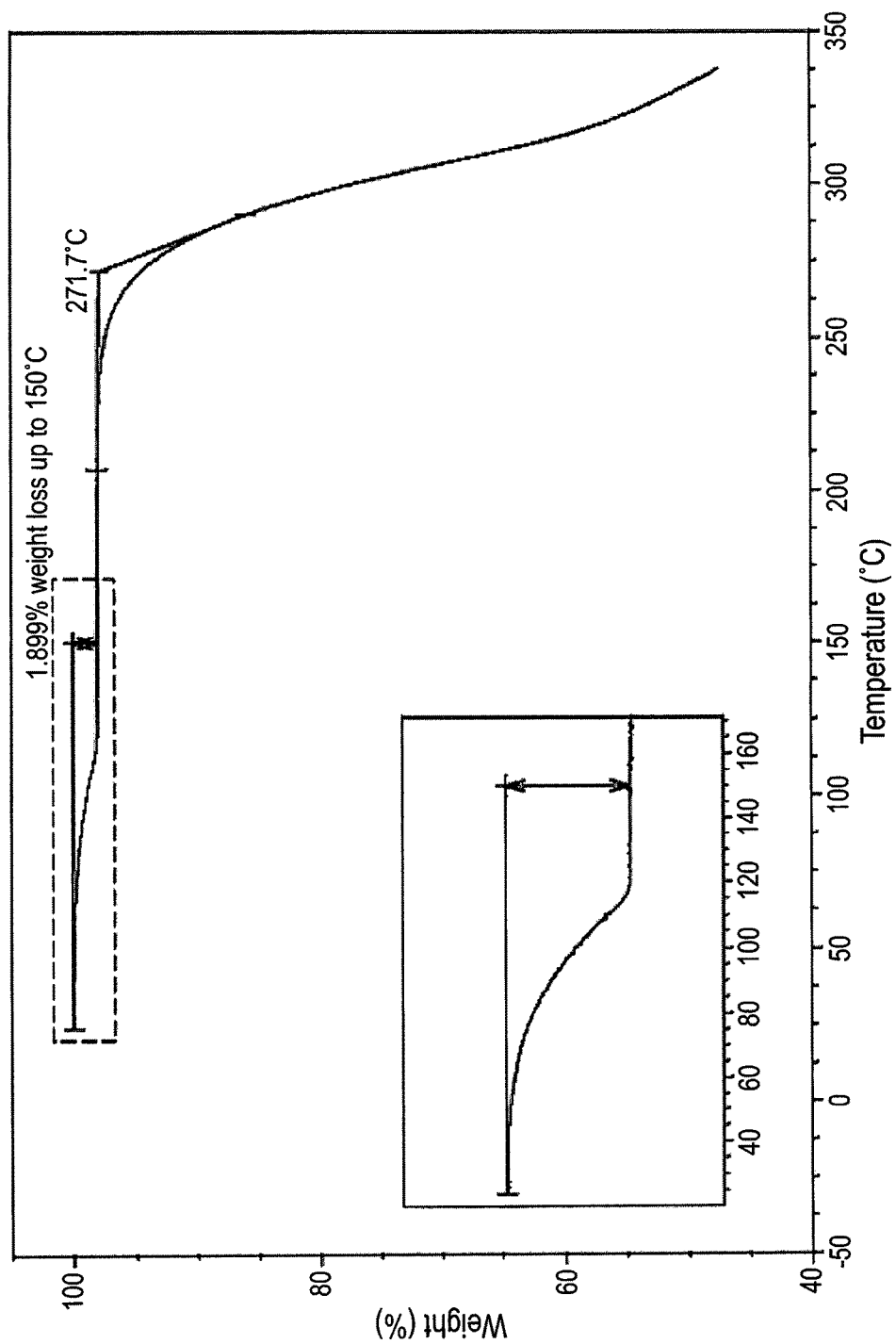
FIG. 7 shows thermal gravimetric analysis (TGA) profile of crystalline Pattern B.

In some embodiments, thermal gravimetric analysis (TGA) was performed using a TA Instruments 2050 thermogravimetric analyzer. Crystalline Pattern B prepared by Example 7 exhibits a TGA profile as depicted in FIG. 7. The profile graphs about 1.9% weight loss up to 150° C. at a temperature rate of 10° C. per minute, and decomposition at about 272° C., indicating that crystalline Pattern B is a boroxine trimer monohydrate. These temperatures have a variation of ±5° C. depending on the measuring condition.

Figure 8:
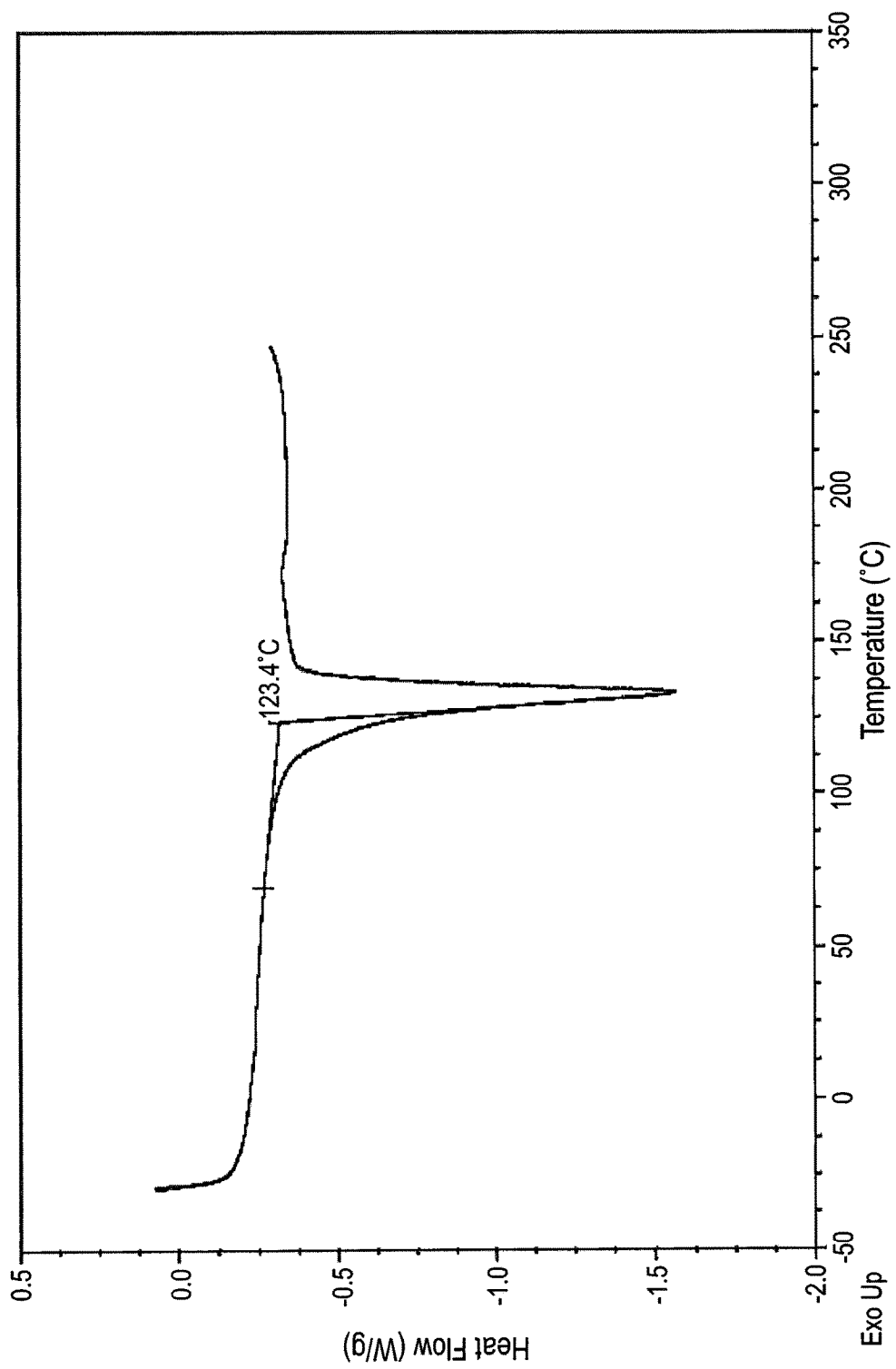
FIG. 8 shows differential scanning calorimetry (DSC) profile of crystalline Pattern B.

In one embodiment, differential scanning calorimetry (DSC) was performed using a TA Instruments Q2000 differential scanning calorimeter. Crystalline Pattern B prepared by Example 7 shows a DSC profile as depicted in FIG. 8. These temperatures have a variation of ±5° C. depending on the measuring condition.

In one embodiment, crystalline Pattern B exhibits an endothermic transition from about 118° C. to about 128° C. In a further embodiment, crystalline Pattern B exhibits an endothermic transition from about 120° C. to about 125° C. In still a further embodiment, crystalline Pattern B exhibits an endothermic transition of about 123.4° C.

In some embodiments, crystalline Pattern B may convert to Pattern F at low temperature. In some embodiments, the low temperature is 150 Kelvin. Pattern F may be a low-temperature form that is likely related to Pattern B through a (thermal) order-disorder phase transition. In some embodiments, Pattern F does not exist at room temperature. In some embodiments, single crystal data was collected on Pattern F at low temperature (150K). In some embodiments, Pattern F comprises boroxine molecule that has two tetrahedral boron atoms, which forms a co-ordinate bond with the carbonyl oxygen as shown by the dashed bond in Formula (1c).

In some embodiments, the present disclosure includes a composition comprising crystalline Pattern B which comprises N,N',N"-[2,4,6-boroxintriyltris[[(1R)-3-methylbutylidene]imino(2-oxo-2,1-ethanediyl)]]tris(2,5-dichlorobenzamide), and a pharmaceutically acceptable carrier.

In some embodiments, the present disclosure includes a composition comprising crystalline Pattern B which comprises N,N',N"-[2,4,6-boroxintriyltris[[(1R)-3-methylbutylidene]imino(2-oxo-2,1-ethanediyl)]]tris(2,5-dichlorobenzamide), or a pharmaceutically acceptable salt thereof, and a therapeutically acceptable carrier (Formula (Ib)).

In some embodiments, the composition comprises at least 80%, 90%, 95%, 98%, 99%, 99.50%, 99.80%, 99.90 or 99.99% of Formula (Ib). In some embodiments, the composition comprises 100% of Formula (Ib).

In some embodiments, the present disclosure includes a composition comprising a mixture of N,N',N"-[2,4,6-boroxintriyltris[[(1R)-3-methylbutylidene]imino(2-oxo-2,1-ethanediyl)]]tris(2,5-dichlorobenzamide), and [(1R)-1-({[(2,5-Dichlorobenzoyl)amino]acetyl}amino)-3-methylbutyl] boronic acid.

In some embodiments, the present disclosure includes a composition comprising a mixture of N,N',N"-[2,4,6-boroxintriyltris[[(1R)-3-methylbutylidene]imino(2-oxo-2,1-ethanediyl)]]tris(2,5-dichlorobenzamide), or a pharmaceutically acceptable salt thereof, and [(1R)-1-({[(2,5-Dichlorobenzoyl)amino]acetyl}amino)-3-methylbutyl] boronic acid, or a pharmaceutically acceptable salt thereof, and a therapeutically acceptable carrier.

In some embodiments, the mixture of the compositions comprise at least 80%, 90%, 95%, 98%, 99%, 99.50%, 99.80%, 99.90 or 99.99% of Formula (Ib). In some embodiments, the mixture of the composition comprises 100% of Formula (Ib).

Crystalline Pattern B may be formulated in a conventional manner using one or more pharmaceutically acceptable excipients.

For oral administration, the pharmaceutical compositions may take the form of capsules or tablets formulated with pharmaceutically acceptable excipients such as filler, lubricant, flow-aid, binder, buffer or bulking agent.

In some embodiments, the filler is powdered cellulose, microcrystalline cellulose, silicified microcrystalline cellulose, low-moisture microcrystalline cellulose, sodium starch glycolate, pregelatinized starch, or mixtures thereof. In other embodiments, the filler is microcrystalline cellulose, sodium starch glycolate, pregelatinized starch, or mixtures thereof. In one embodiment, the filler is microcrystalline cellulose.

In some embodiments, the lubricant is magnesium stearate, glyceryl behenate, hydrogenated vegetable oil, talc, zinc stearate, calcium stearate, sucrose stearate, sodium stearyl fumarate, or mixtures thereof. In one embodiment, the lubricant is magnesium stearate.

In some embodiments, the flow-aid is talc. In some embodiments, the buffer is sodium citrate or citric acid. In some embodiments, the bulking agent is glycine.

In some embodiments, the pharmaceutically acceptable excipients are one or more of microcrystalline cellulose, magnesium stearate, and talc.

The compound of Formula (Ia) and the cyclic trimer Formula (Ib) are selective proteasome inhibitors. As such, crystalline Pattern B and pharmaceutically acceptable compositions thereof are useful for treating a patient having, or at risk of developing or experiencing a recurrence of, a proteasome-mediated disorder.

As used herein, the term "proteasome-mediated disorder" includes any disorder, disease or condition which is caused or characterized by an increase in proteasome expression or activity. The term "proteasome-mediated disorder" also includes any disorder, disease or condition in which inhibition of proteasome activity is beneficial.

For example, crystalline Pattern B or its pharmaceutical compositions are useful for treating disorders mediated via proteins (e.g., NFκB, p27$^{Kip}$, p21$^{WAF/CIP1}$, p53) which are regulated by proteasome activity. Relevant disorders include inflammatory disorders (e.g., rheumatoid arthritis, inflammatory bowel disease, asthma, chronic obstructive pulmonary disease (COPD), osteoarthritis, dermatosis (e.g., atopic dermatitis, psoriasis)), vascular proliferative disorders (e.g., atherosclerosis, restenosis), proliferative ocular disorders (e.g., diabetic retinopathy), benign proliferative disorders (e.g., hemangiomas), autoimmune diseases (e.g., multiple sclerosis, tissue and organ rejection), as well as inflammation associated with infection (e.g., immune responses), antibody-mediated disease, neurodegenerative disorders (e.g., Alzheimer's disease, Parkinson's disease, motor neurone disease, neuropathic pain, triplet repeat disorders, astrocytoma, and neurodegeneration as result of alcoholic liver disease), ischemic injury (e.g., stroke), and cachexia including accelerated muscle protein breakdown that accompanies various physiological and pathological states (e.g., nerve injury, fasting, fever, acidosis, HIV infection, cancer affliction, and certain endocrinopathies), or useful for desensitization therapy.

Non-limiting examples of autoimmune diseases and antibody-mediated diseases include systemic lupus erythematosus, lupus nephritis, Sjogren's syndrome, ulcerative colitis, Crohn's disease, type 1 diabetes, myasthenia gravis, idiopathic pulmonary fibrosis, cirrhosis, endomyocardial fibrosis, scleroderma sclerosis, systemic sclerosis, antibody-mediated rejection, antibody-mediated rejection in organ transplantation, antibody-mediated rejection in kidney transplantation, antibody-mediated rejection in lung transplantation, antibody-mediated rejection in heart transplantation, antibody-mediated rejection in liver transplantation, antibody-mediated rejection in pancreas transplantation, or graft versus host disease.

Crystalline Pattern B or its pharmaceutical compositions are useful for the treatment of cancer. As used herein, the term "cancer" refers to a cellular disorder characterized by uncontrolled or dis-regulated cell proliferation, decreased cellular differentiation, inappropriate ability to invade surrounding tissue, and/or ability to establish new growth at ectopic sites. The term "cancer" includes, but is not limited to, solid tumors and hematologic malignancies. The term "cancer" encompasses diseases of skin, tissues, organs, bone, cartilage, blood, and vessels. The term "cancer" further encompasses primary and metastatic cancers.

Non-limiting examples of solid tumors that can be treated with the disclosed proteasome inhibitors or pharmaceutical compositions include pancreatic cancer; bladder cancer; colorectal cancer; breast cancer, including metastatic breast cancer; prostate cancer, including androgen-dependent and androgen-independent prostate cancer; renal cancer, including, e.g., metastatic renal cell carcinoma; hepatocellular cancer; lung cancer, including, e.g., non-small cell lung cancer (NSCLC), bronchioloalveolar carcinoma (BAC), and adenocarcinoma of the lung; ovarian cancer, including, e.g., progressive epithelial or primary peritoneal cancer; cervical cancer; gastric cancer; esophageal cancer; head and neck cancer, including, e.g., squamous cell carcinoma of the head and neck; melanoma; neuroendocrine cancer, including metastatic neuroendocrine tumors; brain tumors, including, e.g., glioma, anaplastic oligodendroglioma, adult glioblastoma multiforme, and adult anaplastic astrocytoma; bone cancer; and soft tissue sarcoma.

Non-limiting examples of hematologic malignancies that can be treated with the disclosed proteasome inhibitors or pharmaceutical compositions include acute myeloid leukemia (AML); chronic myelogenous leukemia (CML), including accelerated CIVIL and CIVIL blast phase (CIVIL-BP); acute lymphoblastic leukemia (ALL); chronic lymphocytic leukemia (CLL); Hodgkin's disease (HD); lymphoma; non-Hodgkin's lymphoma (NHL), including follicular lymphoma and mantle cell lymphoma; B-cell lymphoma; T-cell lymphoma; multiple myeloma (MM); Waldenstrom's macroglobulinemia; myelodysplastic syndromes (MDS), including refractory anemia (RA), refractory anemia with ringed sideroblasts (RARS), (refractory anemia with excess blasts (RAEB), and RAEB in transformation (RAEB-T); and myeloproliferative syndromes.

In some embodiments, crystalline Pattern B or its pharmaceutical compositions thereof are useful in treatment of amyloidosis.

In some embodiments, crystalline Pattern B or its pharmaceutical compositions thereof are used to treat a patient having or at risk of developing or experiencing a recurrence (relapse) in a cancer selected from multiple myeloma and mantle cell lymphoma.

In some embodiments, crystalline Pattern B or its pharmaceutical compositions are used to treat a patient with refractory mantle cell lymphoma.

In some embodiments, crystalline Pattern B or its pharmaceutical compositions are used to treat a patient with refractory multiple myeloma.

In some embodiments, crystalline Pattern B or its pharmaceutical compositions are administered with one or more therapeutic agents. The other therapeutic agents may also inhibit the proteasome, or may operate by a different mechanism. In some embodiments, the other therapeutic agents are those that are normally administered to patients with the disease or condition being treated. Crystalline Pattern B may be administered with the other therapeutic agent(s) in a single dosage form or as a separate dosage form. When administered as a separate dosage form, the other therapeutic agent(s) may be administered prior to, at the same time as, or following administration of crystalline Pattern B.

In some embodiments, crystalline Pattern B or the pharmaceutical compositions thereof are administered with one or more anticancer agent(s). As used herein, the term "anticancer agents" refers to any agent that is administered to a patient with cancer for purposes of treating the cancer.

In some embodiments, the other therapeutic agent includes DNA damaging chemotherapeutic agents such as topoisomerase I inhibitors (e.g., irinotecan, topotecan, camptothecin and analogs or metabolites thereof, and doxorubicin); topoisomerase II inhibitors (e.g., etoposide, teniposide, and daunorubicin); alkylating agents (e.g., melphalan, chlorambucil, busulfan, thiotepa, ifosfamide, carmustine, lomustine, semustine, streptozocin, decarbazine, methotrexate, mitomycin C, and cyclophosphamide); DNA intercalators (e.g., cisplatin, oxaliplatin, and carboplatin); DNA intercalators and free radical generators such as bleomycin; and nucleoside mimetics (e.g., 5-fluorouracil, capecitibine, gemcitabine, fludarabine, cytarabine, mercaptopurine, thioguanine, pentostatin, and hydroxyurea).

In some embodiments, the other therapeutic agent includes chemotherapeutic agents that disrupt cell replication such as: paclitaxel, docetaxel, and related analogs; vincristine, vinblastin, and related analogs; thalidomide, lenalidomide, and related analogs (e.g., CC-5013 and CC-4047); protein tyrosine kinase inhibitors (e.g., imatinib mesylate and gefitinib); proteasome inhibitors (e.g., bortezomib); NF-κB inhibitors, including inhibitors of IκB kinase; antibodies which bind to proteins overexpressed in cancers and thereby downregulate cell replication (e.g., trastuzumab, rituximab, cetuximab, and bevacizumab); and other inhibitors of proteins or enzymes known to be upregulated, over-expressed or activated in cancers, the inhibition of which down-regulates cell replication.

In some embodiments, crystalline Pattern B or its pharmaceutical composition is administered with lenalidomide.

In some embodiments, crystalline Pattern B or its pharmaceutical composition is administered with melphalan.

In some embodiments, crystalline Pattern B or its pharmaceutical composition is administered with cyclophosphamide.

In some embodiments, crystalline Pattern B or its pharmaceutical composition is administered with dexamethasone.

In some embodiments, crystalline Pattern B or its pharmaceutical composition is administered with cyclophosphamide and dexamethasone.

In some embodiments, crystalline Pattern B or its pharmaceutical composition is administered with lenalidomide and dexamethasone.

The following Examples illustrate the preparation of crystalline Pattern B of the present disclosure but it is not limited to the details thereof.

Example 1

To a solution comprising N,N',N"-[2,4,6-boroxintriyltris [[(1R)-3-methylbutylidene]imino(2-oxo-2,1-ethanediyl)]] tris(2,5-dichlorobenzamide) in ethyl acetate, an equivalent mole of methyl cinnamate was added (1:1). The mixture was stirred at room temperature overnight. White solids were collected by filtration, washed with suitable solvent and dried in vacuo providing crystalline Pattern B with residual methyl cinnamate. $^1$H NMR analysis indicated that the molar ratio of crystalline Pattern B to the residual methyl cinnamate was about 10:3.

The indexed Powder x-ray diffraction patterns (XRPD) for crystalline Pattern B was collected with a PANalytical X'Pert PRO MPD diffractometer using an incident beam of Cu radiation produced using an Optix long, fine-focus source. An elliptically graded multilayer mirror was used to focus Cu Kα X-rays through the specimen and onto the detector. Prior to the analysis, a silicon specimen (NIST SRM 640d) was analyzed to verify the observed position of the Si 111 peak is consistent with the NIST-certified position. A specimen of the sample was sandwiched between 3-μm-thick films and analyzed in transmission geometry. A beam-stop, short antiscatter extension, and an antiscatter knife edge were used to minimize the background generated by air. Soller slits for the incident and diffracted beams were used to minimize broadening from axial divergence. Diffraction patterns were collected using a scanning position-sensitive detector (X'Celerator) located 240 mm from the specimen and Data Collector software v. 2.2b.

FIG. 1 shows an indexing solution of XRPD pattern for crystalline Pattern B collected from Example 1.

Figure 4:
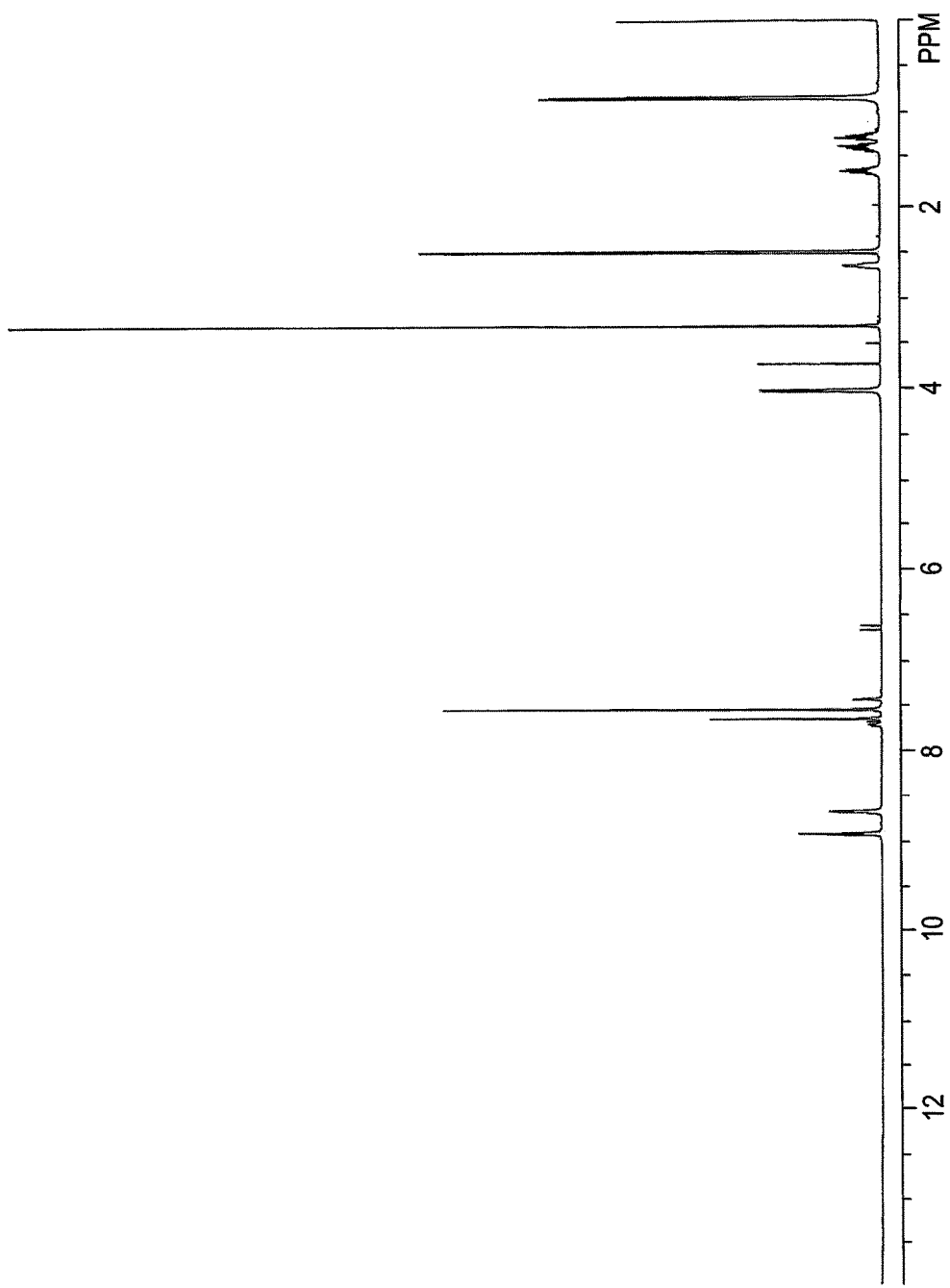
FIG. 4 shows $^1$H NMR spectrum of crystalline Pattern B collected from Example 1.

FIG. 4 shows $^1$H NMR spectrum of crystalline Pattern B collected from Example 1.

Example 2

To a solution comprising N,N',N"-[2,4,6-boroxintriyltris[[(1R)-3-methylbutylidene]imino(2-oxo-2,1-ethanediyl)]]tris(2,5-dichlorobenzamide) in ethyl acetate, an equivalent mole of methyl benzoate was added (1:1). The mixture was stirred at room temperature overnight. White solids were collected by filtration, washed with suitable solvent and dried in vacuo providing crystalline Pattern B.

X-ray powder diffraction pattern is consistent with FIG. 1.

Example 3

To a solution comprising N,N',N"-[2,4,6-boroxintriyltris[[(1R)-3-methylbutylidene]imino(2-oxo-2,1-ethanediyl)]]tris(2,5-dichlorobenzamide) in ethyl acetate, an equivalent mole of anethole was added (1:1). The mixture was stirred at room temperature overnight. White solids were collected by filtration, washed with suitable solvent and dried in vacuo providing crystalline Pattern B.

X-ray powder diffraction pattern is consistent with FIG. 1.

Example 4

To a solution comprising N,N',N"-[2,4,6-boroxintriyltris[[(1R)-3-methylbutylidene]imino(2-oxo-2,1-ethanediyl)]]tris(2,5-dichlorobenzamide) in ethyl acetate, an equivalent mole of triacetin was added (1:1). The mixture was stirred at room temperature overnight. White solids were collected by filtration, washed with suitable solvent and dried in vacuo providing crystalline Pattern B.

X-ray powder diffraction pattern is consistent with FIG. 1.

Example 5

To a solution comprising N,N',N"-[2,4,6-boroxintriyltris[[(1R)-3-methylbutylidene]imino(2-oxo-2,1-ethanediyl)]]tris(2,5-dichlorobenzamide) in ethyl acetate, an equivalent mole of triethyl citrate was added (1:1). The mixture was stirred at room temperature overnight. White solids were collected by filtration, washed with suitable solvent and dried in vacuo providing crystalline Pattern B.

X-ray powder diffraction pattern is consistent with FIG. 1.

Example 6

To a solution comprising 80 mg of N,N',N"-[2,4,6-boroxintriyltris[[(1R)-3-methylbutylidene]imino(2-oxo-2,1-ethanediyl)]]tris(2,5-dichlorobenzamide) in 1 mL of ethyl acetate (80 mg/mL), 6 mg of crystalline Pattern B resulting from EXAMPLE 1 was added at room temperature. The solution was stirred overnight. White solids were collected by filtration, washed with suitable solvent and dried in vacuo providing approximately 50 mg of crystalline Pattern B.

Figure 10:
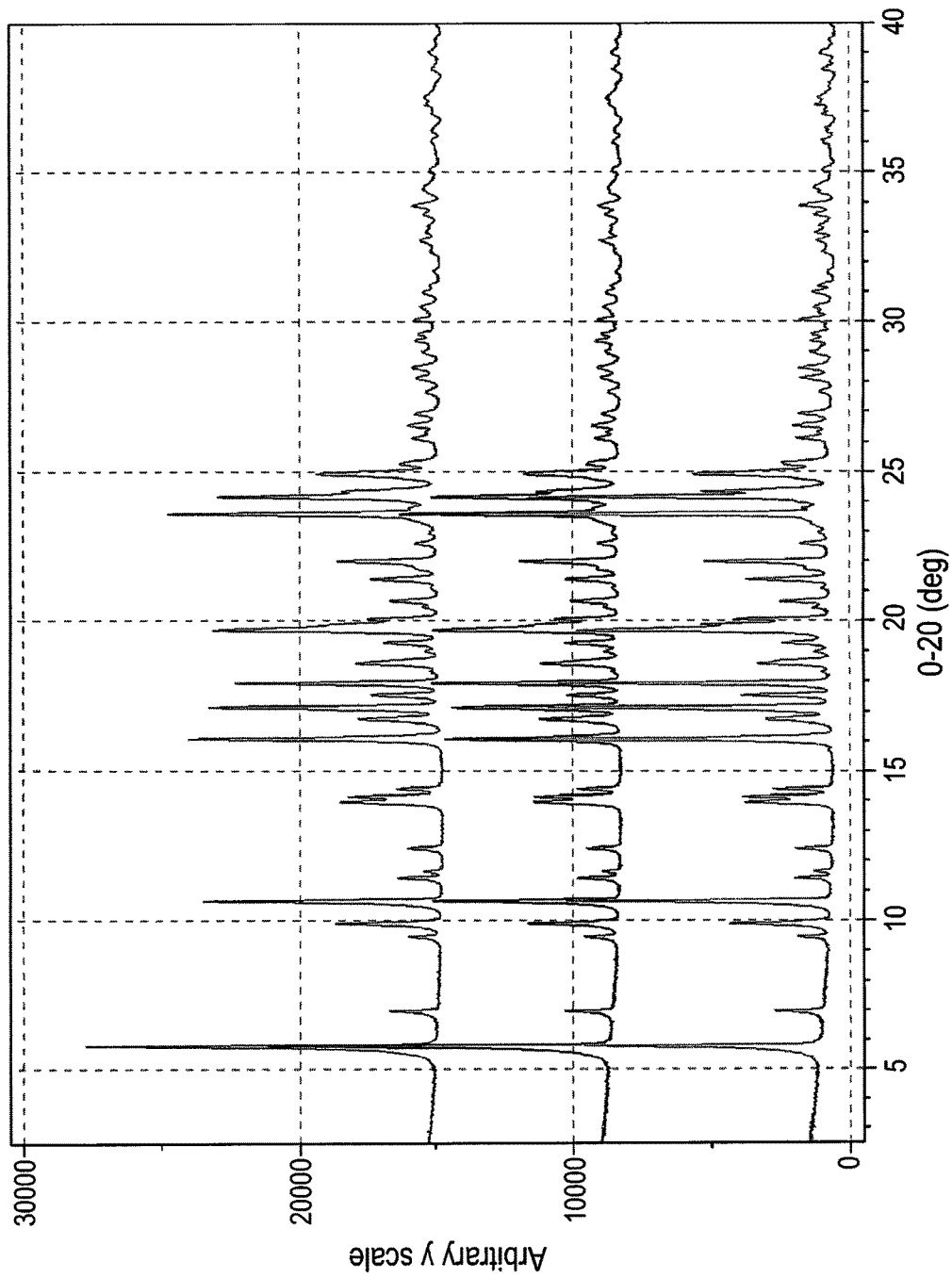
FIG. 10 shows three XRPDs of crystalline Pattern B. The XRPD of crystalline Pattern B isolated from Example 7 is at the top. The XRPD of crystalline Pattern B isolated from Example 6 is at the middle. The XRPD of crystalline Pattern B isolated from Example 1 is at the bottom.

FIG. 10 shows three XRPDs of crystalline Pattern B. The XRPD of crystalline Pattern B isolated from Example 7 is at the top. The XRPD of crystalline Pattern B isolated from Example 6 is at the middle. The XRPD of crystalline Pattern B isolated from Example 1 is at the bottom.

Example 7

Six milliliters (6 mL) of ethyl acetate was added in a vial containing 479.9 mg non-crystalline solid comprising the compound of Formula (Ib) under nitrogen flow. The vial was capped and a sample was sonicated in a water bath, resulting in a clear solution. The solution was transferred into a vial containing 9.8 mg of crystalline Pattern B, resulted from EXAMPLE 6, under nitrogen flow. The resulting turbid solution was stirred overnight in the closed vial, resulting in a white suspension. White solids were isolated under nitrogen protection with a yield of 374.8 mg of crystalline Pattern B (76.6%). $^1$H NMR analysis indicated that there was no residual methyl cinnamate.

Figure 2:
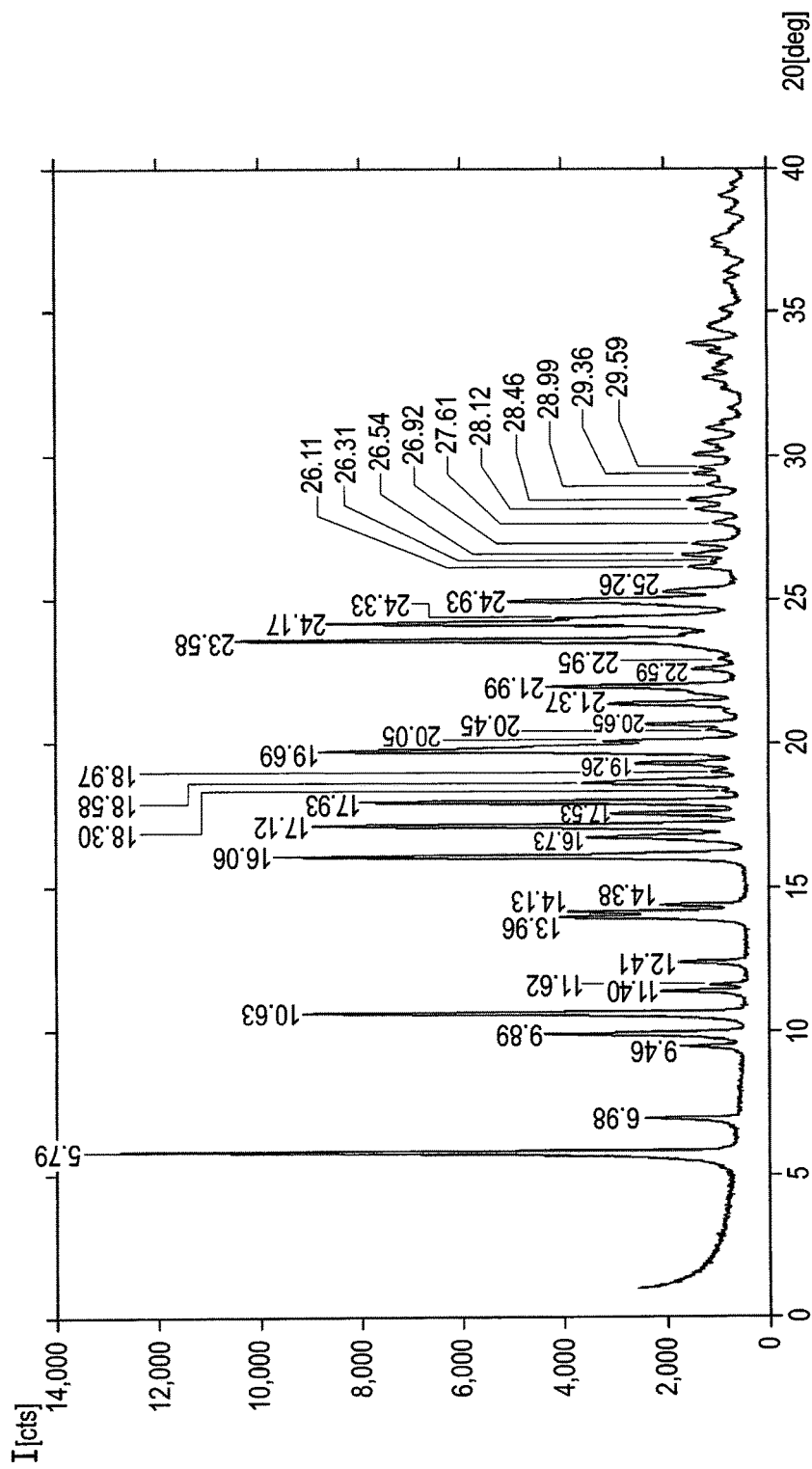
FIG. 2 shows a XRPD pattern with labeled peaks of crystalline Pattern B.

FIG. 2 shows the XRPD pattern with labeled peaks of crystalline Pattern B collected from Example 7. Prominent XRPD peaks for crystalline Pattern B are shown below:

| °2θ | d space (Å) | Intensity (%) |
|---|---|---|
| 5.79 ± 0.20 | 15.247 ± 0.526 | 100 |
| 6.98 ± 0.20 | 12.647 ± 0.362 | 18 |
| 9.46 ± 0.20 | 9.345 ± 0.197 | 13 |
| 9.89 ± 0.20 | 8.936 ± 0.180 | 33 |
| 10.63 ± 0.20 | 8.316 ± 0.156 | 70 |
| 11.40 ± 0.20 | 7.758 ± 0.136 | 16 |
| 12.41 ± 0.20 | 7.129 ± 0.114 | 13 |
| 13.96 ± 0.20 | 6.341 ± 0.090 | 32 |
| 14.13 ± 0.20 | 6.262 ± 0.088 | 29 |
| 14.38 ± 0.20 | 6.155 ± 0.085 | 16 |
| 16.06 ± 0.20 | 5.514 ± 0.068 | 75 |
| 16.73 ± 0.20 | 5.294 ± 0.063 | 27 |
| 17.12 ± 0.20 | 5.175 ± 0.060 | 68 |
| 17.53 ± 0.20 | 5.055 ± 0.057 | 23 |
| 17.93 ± 0.20 | 4.944 ± 0.055 | 61 |
| 18.58 ± 0.20 | 4.773 ± 0.051 | 28 |
| 19.26 ± 0.20 | 4.605 ± 0.047 | 20 |
| 19.69 ± 0.20 | 4.505 ± 0.045 | 68 |
| 20.05 ± 0.20 | 4.426 ± 0.044 | 25 |
| 20.65 ± 0.20 | 4.299 ± 0.041 | 18 |
| 21.37 ± 0.20 | 4.154 ± 0.038 | 24 |
| 21.99 ± 0.20 | 4.040 ± 0.036 | 33 |
| 22.59 ± 0.20 | 3.933 ± 0.034 | 11 |
| 23.58 ± 0.20 | 3.770 ± 0.032 | 80 |
| 24.17 ± 0.20 | 3.680 ± 0.030 | 67 |
| 24.33 ± 0.20 | 3.655 ± 0.030 | 32 |
| 24.93 ± 0.20 | 3.569 ± 0.028 | 39 |
| 25.26 ± 0.20 | 3.523 ± 0.027 | 15 |
| 26.11 ± 0.20 | 3.410 ± 0.026 | 12 |
| 26.54 ± 0.20 | 3.356 ± 0.025 | 13 |
| 26.92 ± 0.20 | 3.309 ± 0.024 | 11 |
| 28.12 ± 0.20 | 3.171 ± 0.022 | 11 |
| 28.46 ± 0.20 | 3.134 ± 0.022 | 11 |
| 29.36 ± 0.20 | 3.040 ± 0.020 | 11 |
| 29.59 ± 0.20 | 3.016 ± 0.020 | 10 |

Figure 3:
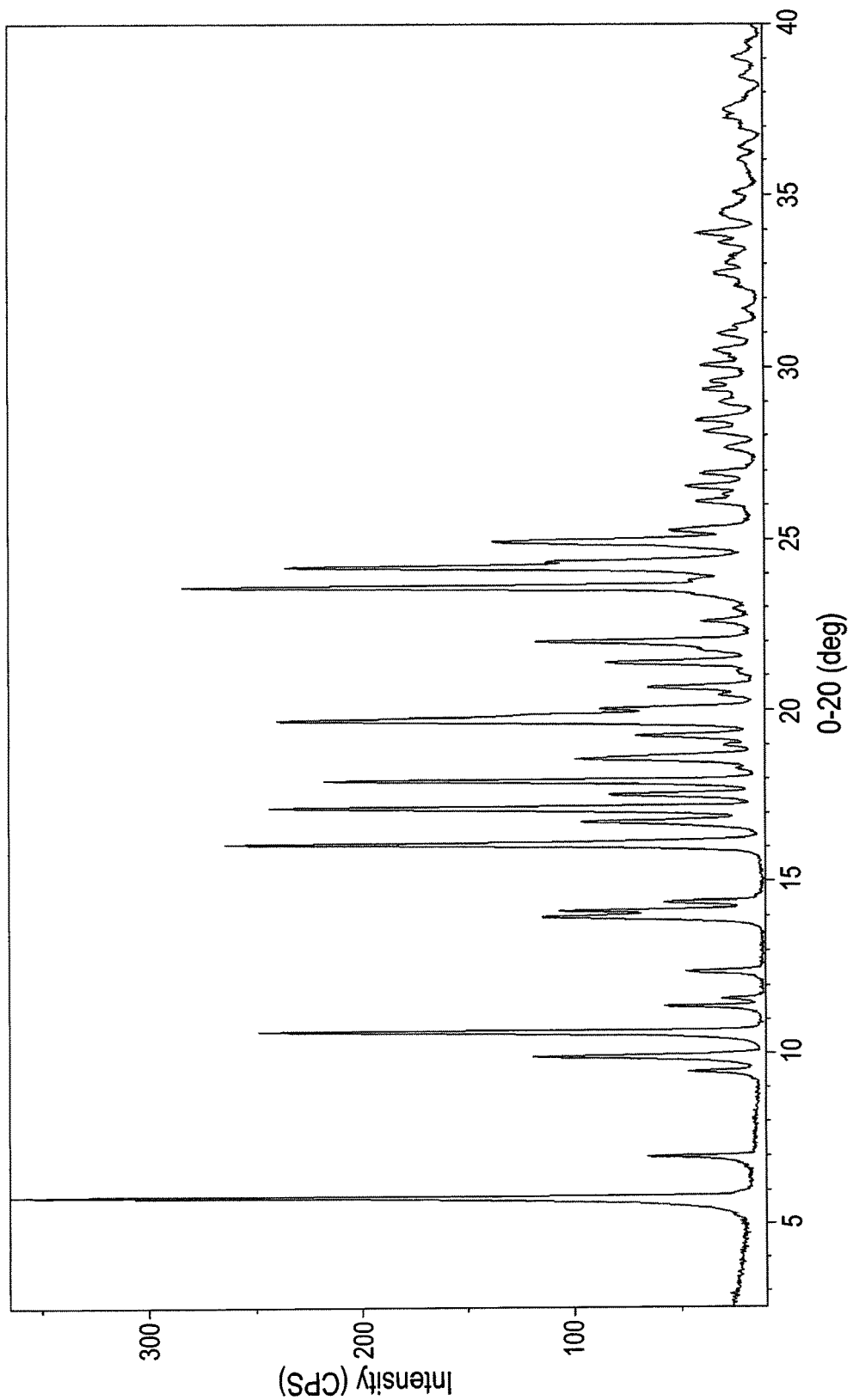
FIG. 3 shows a XRPD pattern of crystalline Pattern B.

FIG. 3 shows the XRPD pattern without label of crystalline Pattern B collected from Example 7.

Figure 11:
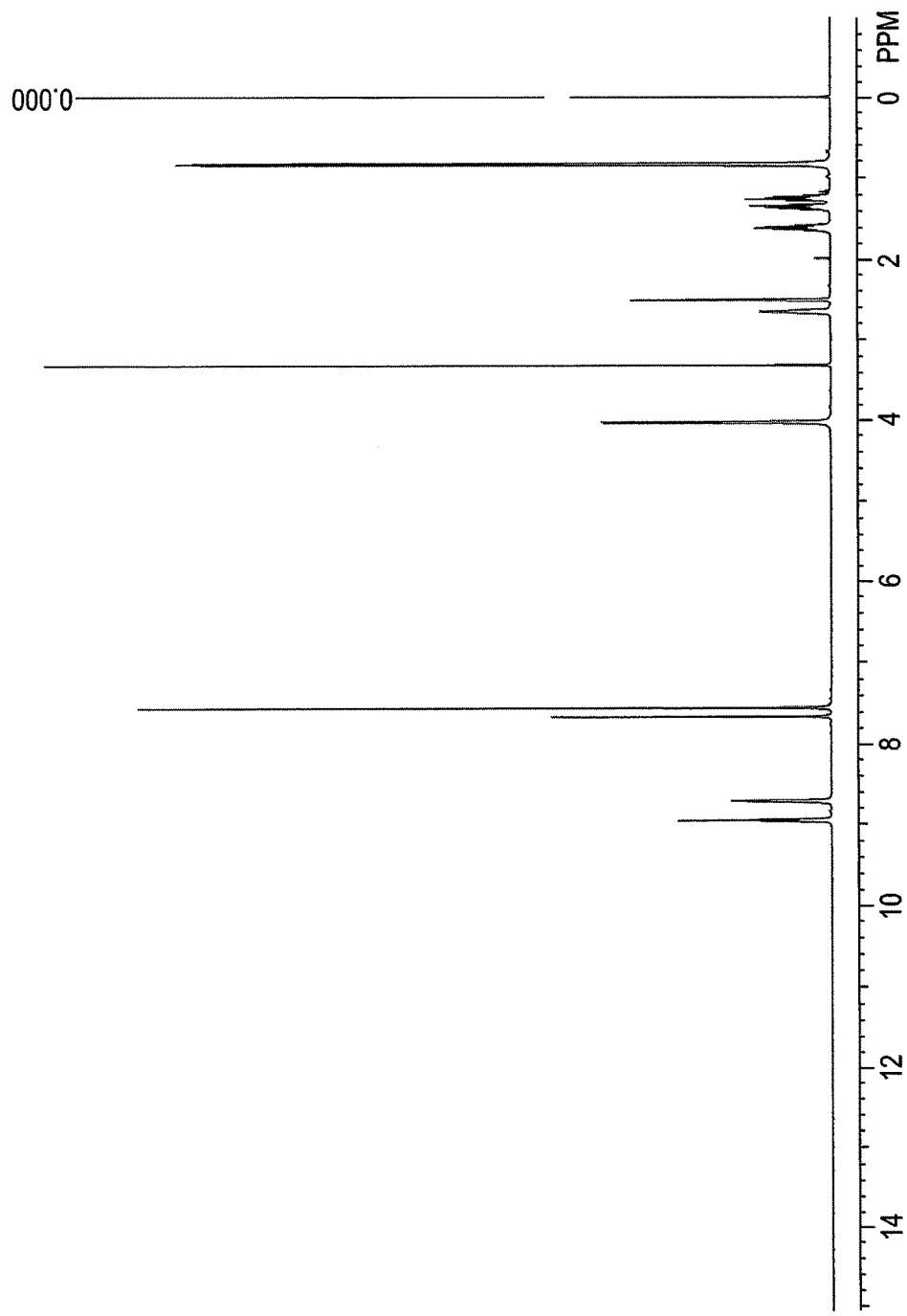
FIG. 11 shows $^1$H NMR spectrum of crystalline Pattern B collected from Example 7.

FIG. 11 shows $^1$H NMR spectrum of crystalline Pattern B collected from Example 7.

Figure 5:
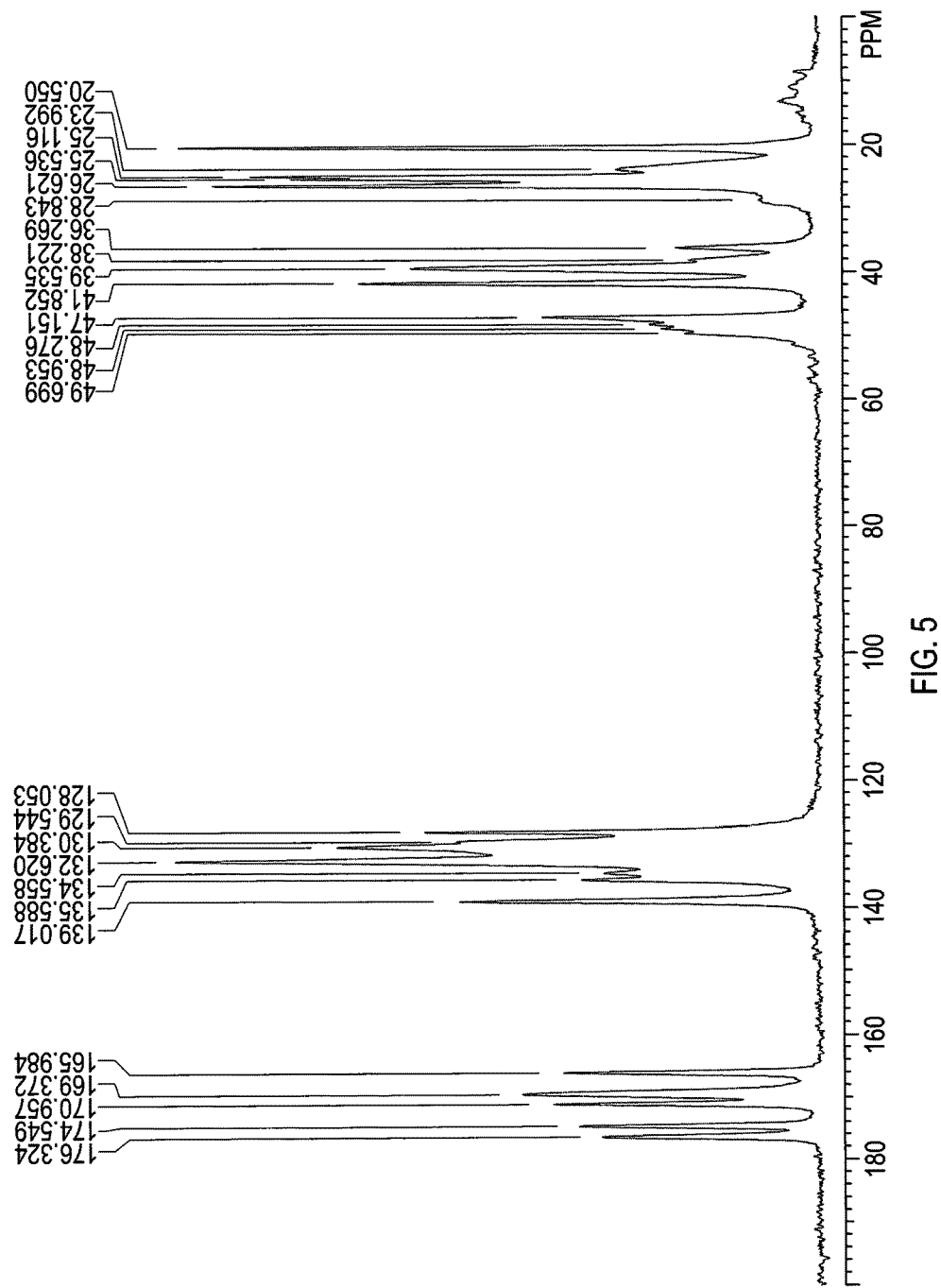
FIG. 5 shows solid state carbon-13 nuclear magnetic resonance spectrum of crystalline Pattern B.

FIG. 5 shows solid state carbon-13 nuclear magnetic resonance spectrum of crystalline Pattern B collected from Example 7.

Figure 6:
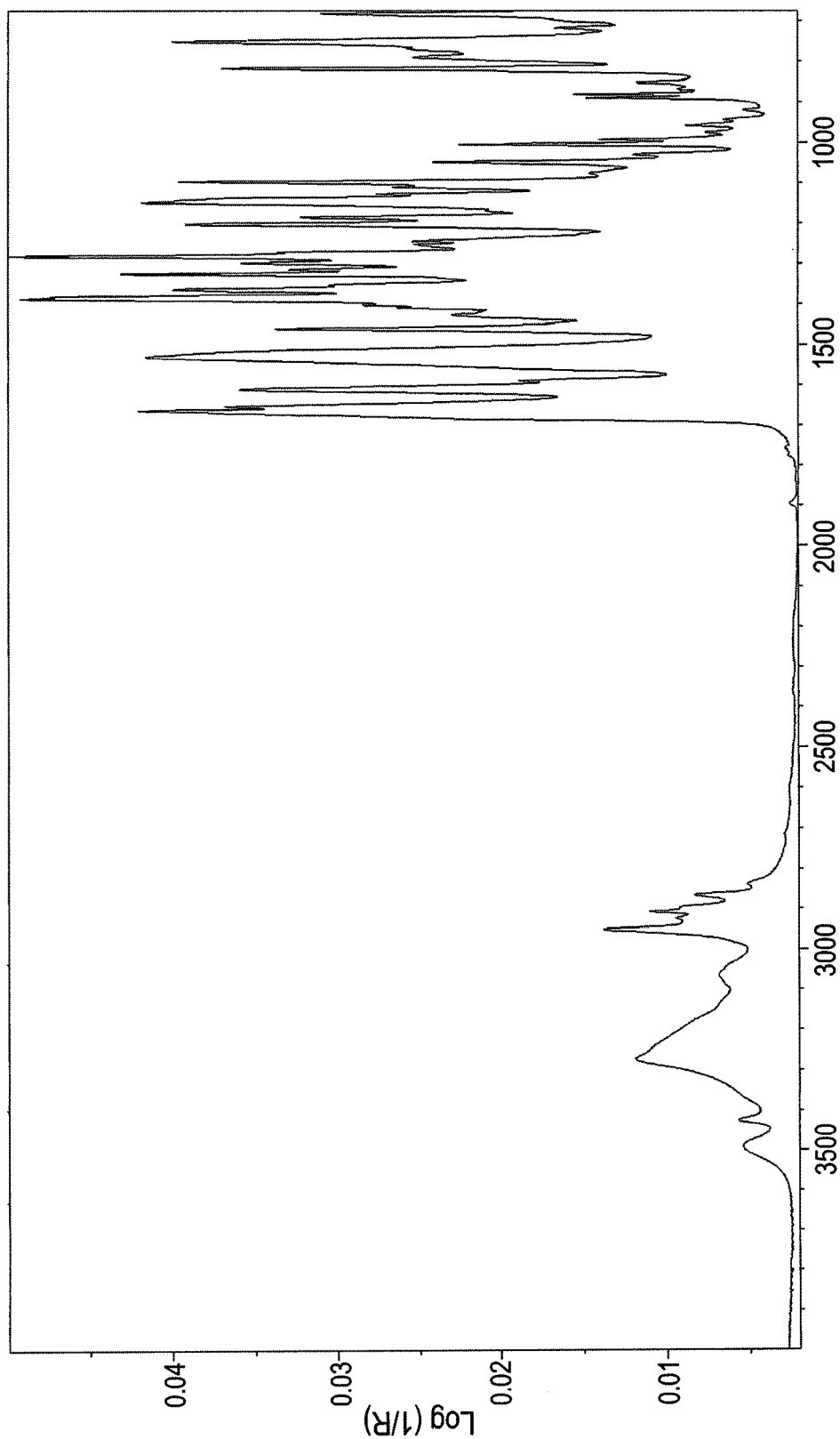
FIG. 6 shows IR spectrum of crystalline Pattern B.

FIG. 6 shows IR spectrum of crystalline Pattern B collected from Example 7.

FIG. 7 shows thermal gravimetric analysis (TGA) profile of crystalline Pattern B collected from Example 7.

Thermogravimetric analysis was performed using a TA Instruments 2050 thermogravimetric analyzer. Temperature calibration was performed using nickel and Alumel™. The sample was placed in a platinum pan and inserted into the TG furnace. The furnace was heated under a nitrogen purge. The sample was heated from 25° C. to 350° C., at 10° C./min (abbreviated "00-350-10").

FIG. 8 shows differential scanning calorimetry (DSC) profile of crystalline Pattern B collected from Example 7.

Differential scanning calorimetry was performed using a TA Instruments Q2000 differential scanning calorimeter. Temperature calibration was performed using NIST-traceable indium metal. The sample was placed into an aluminum DSC pan, covered with a lid, and the weight was accurately recorded. (A Tzero crimped pan with a manual pinhole, abbreviated "TOCMP" was used.) A weighed aluminum pan configured as the sample pan was placed on the reference side of the cell. The sample was heated from −30° C. to 250° C., at 10° C./min. (abbreviated "(−30)–250–10").

Figure 9:
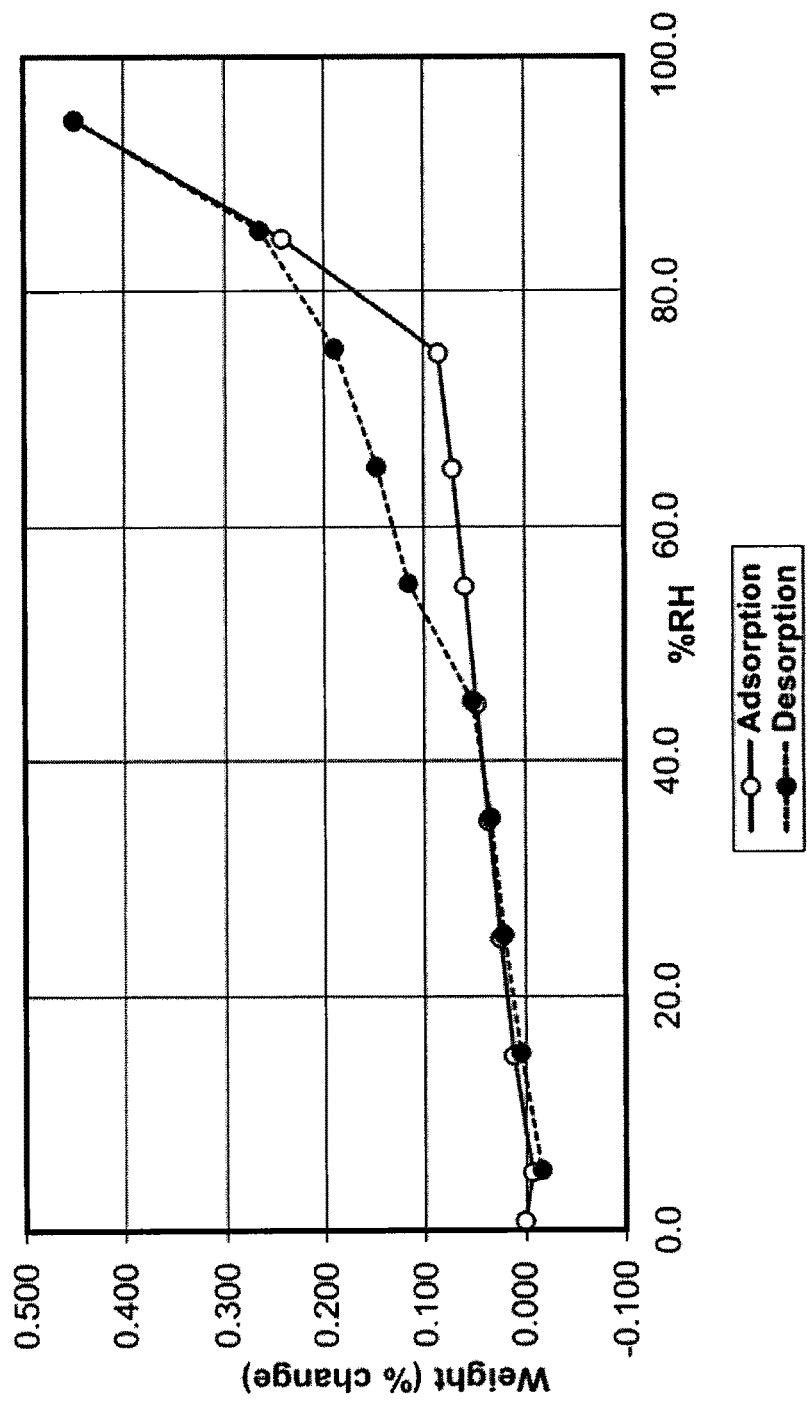
FIG. 9 shows dynamic vapor sorption (DVS) analysis (weight % vs relative humidity).

FIG. 9 shows dynamic vapor sorption (DVS) analysis (weight % vs relative humidity) collected from Example 7.

Dynamic vapor sorption/desorption data were collected on a VTI SGA-100 Vapor Sorption Analyzer. NaCl and PVP were used as calibration standards. The sample was not dried prior to analysis. Sorption and desorption data were collected over a range from 5% to 95% RH at 10% RH increments under a nitrogen purge. The equilibrium criterion used for analysis was less than 0.0100% weight change in five minutes with a maximum equilibration time of three hours. Data were not corrected for the initial moisture content of the samples.

Example 8

To a solution comprising N,N',N''-[2,4,6-boroxintriyltris [[(1R)-3-methylbutylidene]imino(2-oxo-2,1-ethanediyl)]] tris(2,5-dichlorobenzamide) in ACN in a small vial was seeded with crystalline Pattern B. The solution concentration was about 7 mg/mL. The small vial was then placed inside a larger vessel containing $H_2O$ (anti-solvent). The small vial was left open, and the large container was covered to allow vapor diffusion to occur. Needles with birefringence/extinctions were observed on the side of the small vial after 6 days, which appeared to be of good quality as observed by optical microscopy.

Indexing was performed on the single crystal data for a single crystal from this sample. This resulted in the unit cell parameters at room temperature. This unit cell was found to be consistent with the indexing solution for powder Pattern B.

Table 2 shows unit cell parameters determined for the single crystal from this sample.

TABLE 2

| Single Crystal Indexing | |
|---|---|
| Pattern | B |
| Temperature | Ambient |
| Space Group | $P2_1$ |
| a (Å) | 15.5076 |
| b (Å) | 11.0251 |
| c (Å) | 15.9090 |
| α (°) | 90 |
| β (°) | 107.07 |
| γ (°) | 90 |
| V (Å$^3$) | 2600.2 |

Example 9

To a solution comprising N,N',N''-[2,4,6-boroxintriyltris [[(1R)-3-methylbutylidene]imino(2-oxo-2,1-ethanediyl)]] tris(2,5-dichlorobenzamide) in ACN in a small vial was added a drop of EtOAc containing needle-like crystalline Pattern B. The solution concentration was about 11 mg/mL. The small vial was then placed inside a larger vessel containing $H_2O$ (anti-solvent). The small vial was left open but covered with Al foil with one pin-hole, and the large container was covered to allow vapor diffusion to occur. Needles with birefringence/extinctions and aggregates of needles were observed on the side of the small vial after 7 days, which appeared to be of good quality as observed by optical microscopy.

Single crystal data was collected at 150 K on a single crystal from this sample. A colorless needle of this example having approximate dimensions of 0.20×0.08×0.02 mm was mounted on a fiber in random orientation. Preliminary examination and data collection were performed with Cu Kα radiation (λ=1.54178 Å) on a Rigaku Rapid II diffractometer equipped with confocal optics. Refinements were performed using SHELX2013 (Sheldrick, G. M. Acta Cryst., 2008, A64, 112).

Cell constants and an orientation matrix for data collection were obtained from least-squares refinement using the setting angles of 17999 reflections in the range 3°<θ<61°. The refined mosaicity from DENZO/SCALEPACK is 0.30° indicating good crystal quality (Otwinowski, Z.; Minor, W. Methods Enzymol. 1997, 276, 307). The space group was determined by the program XPREP (Bruker, XPREP in SHELXTL v. 6.12., Bruker AXS Inc., Madison, Wis., USA, 2002). From the systematic presence of the following conditions: 0k0 k=2n, and from subsequent least-squares refinement, the space group was determined to be $P2_1$ (no. 4).

The data were collected to a maximum diffraction angle, 2θ, of 122.32°, at a temperature of 150 K.

Frames were integrated with HKL3000. A total of 17999 reflections were collected, of which 10851 were unique. Lorentz and polarization corrections were applied to the data. The linear absorption coefficient is 3.625 mm$^{-1}$ for Cu Kα radiation. An empirical absorption correction using SCALEPACK was applied. Transmission coefficients ranged from 0.028 to 0.930. Intensities of equivalent reflections were averaged. The agreement factor for the averaging was 10.3% based on intensity.

The structure was solved by direct methods using SHELXT. The remaining atoms were located in succeeding difference Fourier syntheses. Hydrogen atoms were included in the refinement but restrained to ride on the atom to which they are bonded. The structure was refined in full-matrix least-squares by minimizing the function:

$$\Sigma w(|F_o|^2-|F_c|^2)^2$$

The weight w is defined as $1/[\sigma^2(F_o^2)+(0.2000P)^2+(0.0000P)]$, where $P=(F_o^2+2F_c^2)/3$.

Scattering factors were taken from the "International Tables for Crystallography" (International Tables for Crystallography, Vol. C, Kluwer Academic Publishers: Dordrecht, The Netherlands, 1992, Tables 4.2.6.8 and 6.1.1.4.). Of the 17999 reflections used in the refinements, only the reflections with $F_o^2>2\sigma(F_o^2)$ were used in calculating the fit residual, R. A total of 10851 reflections were used in the calculation. The final cycle of refinement included 765 variable parameters and converged with unweighted and weighted agreement factors of:

$$R=\Sigma|F_o-F_c|/\Sigma F_o=0.1389$$

$$R_w=\sqrt{(\Sigma w(F_o^2-F_c^2)^2/\Sigma w(F_o^2)^2)}=0.3221$$

The standard deviation of an observation of unit weight (goodness of fit) was 1.267. The highest peak in the final difference Fourier had a height of 2.923 e/Å$^3$. The minimum negative peak had a height of −0.624 e/Å$^3$.

Table 3 shows the unit cell parameters determined for the single crystal from this sample.

TABLE 3

| Single Crystal Indexing | |
|---|---|
| Pattern | F |
| Temperature | 150 K |
| Space Group | P2$_1$ |
| a (Å) | 15.4482 |
| b (Å) | 32.7112 |
| c (Å) | 15.7700 |
| α (°) | 90 |
| β (°) | 108.242 |
| γ (°) | 90 |
| V (Å$^3$) | 7568.5 |

Table 4 shows the atomic coordinates and their estimated standard deviations for Pattern F. Table 5 shows the bond distances in Angstroms for Pattern F. Table 6 shows the bond angles in degrees for Pattern F. Table 7 shows Anisotropic Temperature Factor Coefficients for Pattern F.

TABLE 4

Atomic Coordinates and Their Estimated Standard Deviations for Ixazomib Pattern F

| | x | y | z | U(eq) |
|---|---|---|---|---|
| Cl(1) | 6024(4) | 1388(1) | 3505(3) | 45(1) |
| Cl(2) | 538(5) | 3216(2) | 8821(4) | 86(2) |
| Cl(3) | 3232(4) | 1753(2) | 9563(4) | 83(2) |
| Cl(4) | −100(4) | 338(2) | 1558(4) | 71(2) |
| Cl(5) | 3134(3) | 1543(1) | 1971(4) | 44(1) |
| Cl(6) | 4481(4) | 2692(2) | 538(3) | 60(2) |
| Cl(7) | 4008(4) | −308(1) | 6574(3) | 54(2) |
| Cl(8) | 9071(6) | 1645(2) | 1176(4) | 114(3) |
| Cl(9) | 6643(4) | 95(2) | 445(4) | 84(2) |
| Cl(10) | 9744(4) | −1507(2) | 8517(4) | 85(2) |
| Cl(11) | 6835(3) | −133(1) | 7988(4) | 46(1) |
| Cl(12) | 5212(4) | 1053(2) | 9458(3) | 54(2) |
| Cl(13) | 4153(5) | 3033(2) | 6744(4) | 76(2) |
| Cl(14) | 9762(4) | 1817(2) | 8691(4) | 76(2) |
| Cl(15) | 6973(4) | 3238(2) | 8264(4) | 58(2) |
| Cl(16) | 7040(4) | 3954(2) | 1760(4) | 72(2) |
| Cl(17) | 9406(5) | 4732(2) | −328(4) | 87(2) |
| Cl(18) | 5339(4) | 4422(2) | 9541(3) | 59(2) |
| O(1) | 4365(9) | 1950(4) | 3955(8) | 45(3) |
| O(2) | 5972(8) | 1968(3) | 5925(7) | 31(3) |
| O(3) | 2847(7) | 2000(3) | 5887(6) | 17(2) |
| O(4) | 1428(7) | 2212(3) | 6104(7) | 22(3) |
| O(5) | 1964(7) | 3091(3) | 7208(7) | 25(3) |
| O(6) | 1609(6) | 1522(3) | 5652(6) | 12(2) |
| O(7) | 2188(7) | 893(3) | 5119(7) | 19(3) |
| O(8) | 675(8) | 512(3) | 3505(7) | 30(3) |
| O(9) | 3177(7) | 1308(3) | 6319(7) | 18(3) |
| O(10) | 5560(9) | 283(4) | 6117(9) | 49(4) |
| O(11) | 3968(8) | 319(3) | 4112(7) | 32(3) |
| O(12) | 7133(7) | 328(3) | 4188(7) | 21(3) |
| O(13) | 8548(7) | 540(3) | 3951(7) | 24(3) |
| O(14) | 7938(7) | 1438(3) | 2840(7) | 30(3) |
| O(15) | 8352(6) | −159(3) | 4379(6) | 10(2) |
| O(16) | 7767(7) | −786(3) | 4878(7) | 18(3) |
| O(17) | 9290(8) | −1196(3) | 6556(8) | 34(3) |
| O(18) | 6769(7) | −356(3) | 3717(7) | 20(3) |
| O(19) | 5669(8) | 3621(4) | 6241(8) | 42(3) |
| O(20) | 4036(7) | 3624(3) | 4254(7) | 28(3) |
| O(21) | 6804(7) | 2961(3) | 3855(6) | 18(3) |
| O(22) | 7844(6) | 2557(3) | 5036(6) | 14(2) |
| O(23) | 9326(8) | 2142(3) | 6735(7) | 33(3) |
| O(24) | 8387(6) | 3175(3) | 4432(6) | 14(2) |
| O(25) | 8592(7) | 3865(3) | 3961(7) | 19(2) |
| O(26) | 8064(7) | 4762(3) | 2834(7) | 23(3) |
| O(27) | 7153(7) | 3657(3) | 4187(6) | 17(2) |
| O(28) | −2(8) | 1507(3) | 6001(8) | 34(3) |
| O(29) | 75(8) | 4825(3) | 6055(8) | 37(3) |
| N(1) | 5451(9) | 2440(4) | 4276(9) | 26(3) |
| N(2) | 4621(8) | 2150(3) | 6019(7) | 12(3) |
| N(3) | 862(8) | 2468(4) | 4737(8) | 20(3) |
| N(4) | 621(8) | 2757(3) | 6906(8) | 16(3) |

TABLE 4-continued

Atomic Coordinates and Their Estimated Standard Deviations for Ixazomib Pattern F

| | x | y | z | U(eq) |
|---|---|---|---|---|
| N(5) | 1977(8) | 472(4) | 6098(8) | 19(3) |
| N(6) | 2150(9) | 340(4) | 3873(9) | 24(3) |
| N(7) | 4484(9) | 778(4) | 5785(8) | 21(3) |
| N(8) | 5357(8) | 486(3) | 4054(7) | 12(3) |
| N(9) | 9115(8) | 799(3) | 5309(8) | 17(3) |
| N(10) | 9252(8) | 1097(4) | 3113(8) | 19(3) |
| N(11) | 7979(8) | −1192(4) | 3880(8) | 21(3) |
| N(12) | 7806(9) | −1366(4) | 6098(9) | 26(3) |
| N(13) | 4567(9) | 4110(4) | 5890(9) | 28(4) |
| N(14) | 5396(8) | 3813(4) | 4113(8) | 15(3) |
| N(15) | 7949(8) | 2123(4) | 4022(8) | 19(3) |
| N(16) | 7831(9) | 2001(4) | 6295(8) | 23(3) |
| N(17) | 9141(8) | 4132(3) | 5319(8) | 14(3) |
| N(18) | 9375(8) | 4408(4) | 3129(8) | 20(3) |
| C(1) | 5554(11) | 1747(5) | 2685(11) | 24(4) |
| C(2) | 5116(11) | 2086(5) | 2859(11) | 23(4) |
| C(3) | 4959(12) | 2150(5) | 3740(11) | 29(4) |
| C(4) | 5256(11) | 2555(5) | 5071(11) | 26(4) |
| C(5) | 5291(11) | 2205(5) | 5703(11) | 23(4) |
| C(6) | 4505(10) | 1818(5) | 6577(10) | 21(4) |
| C(7) | 4757(10) | 1954(5) | 7569(10) | 19(4) |
| C(8) | 5751(11) | 2101(5) | 8002(11) | 25(4) |
| C(9) | 6451(11) | 1772(5) | 8106(12) | 31(4) |
| C(10) | 5852(14) | 2286(5) | 8911(13) | 48(6) |
| C(11) | 931(11) | 2481(5) | 5567(10) | 21(4) |
| C(12) | 1399(10) | 2127(4) | 4549(9) | 14(3) |
| C(13) | 2033(10) | 2278(4) | 4036(10) | 19(4) |
| C(14) | 1629(12) | 2484(5) | 3141(11) | 32(4) |
| C(15) | 2369(13) | 2659(6) | 2775(13) | 44(5) |
| C(16) | 1000(14) | 2212(6) | 2473(14) | 56(6) |
| C(17) | 423(11) | 2796(5) | 5943(10) | 21(4) |
| C(18) | 1451(11) | 2870(5) | 7440(11) | 23(4) |
| C(19) | 1668(8) | 2697(3) | 8375(6) | 25(4) |
| C(20) | 1307(8) | 2830(3) | 9030(8) | 49(6) |
| C(21) | 1555(9) | 2638(4) | 9858(7) | 65(7) |
| C(22) | 2164(10) | 2313(4) | 10031(7) | 73(7) |
| C(23) | 2526(8) | 2180(3) | 9376(9) | 55(6) |
| C(24) | 2278(8) | 2371(4) | 8548(7) | 41(5) |
| C(25) | 2109(10) | 530(5) | 5359(11) | 20(4) |
| C(26) | 1899(11) | 848(4) | 6575(10) | 19(4) |
| C(27) | 2399(11) | 829(5) | 7567(11) | 27(4) |
| C(28) | 1729(14) | 710(6) | 8147(14) | 55(6) |
| C(29) | 1147(13) | 1059(6) | 8226(14) | 50(6) |
| C(30) | 2312(15) | 552(7) | 9048(15) | 71(7) |
| C(31) | 2180(12) | 190(5) | 4737(11) | 31(5) |
| C(32) | 1409(12) | 505(5) | 3331(11) | 26(4) |
| C(33) | 1487(11) | 716(5) | 2498(11) | 24(4) |
| C(34) | 827(14) | 659(6) | 1668(14) | 46(5) |
| C(35) | 882(15) | 869(6) | 903(15) | 59(6) |
| C(36) | 1611(14) | 1131(6) | 1019(15) | 55(6) |
| C(37) | 2269(12) | 1195(5) | 1878(12) | 34(5) |
| C(38) | 2179(11) | 984(5) | 2570(11) | 25(4) |
| C(39) | 4788(12) | 2386(6) | 2203(12) | 35(5) |
| C(40) | 4933(12) | 2329(5) | 1344(12) | 34(5) |
| C(41) | 5354(12) | 1982(5) | 1180(12) | 35(5) |
| C(42) | 5696(12) | 1705(6) | 1857(13) | 40(5) |
| C(43) | 4383(11) | 68(5) | 7363(11) | 27(4) |
| C(44) | 4768(11) | 423(5) | 7181(11) | 28(4) |
| C(45) | 4976(11) | 490(5) | 6320(11) | 24(4) |
| C(46) | 4701(11) | 887(5) | 4984(10) | 21(4) |
| C(47) | 4652(11) | 539(5) | 4371(10) | 20(4) |
| C(48) | 5467(10) | 165(5) | 3485(10) | 19(4) |
| C(49) | 5243(10) | 318(5) | 2494(10) | 18(4) |
| C(50) | 4279(10) | 475(5) | 2067(11) | 22(4) |
| C(51) | 3549(11) | 158(5) | 1926(11) | 28(4) |
| C(52) | 4233(12) | 692(5) | 1218(12) | 35(5) |
| C(53) | 9011(10) | 814(4) | 4468(10) | 16(4) |
| C(54) | 8602(10) | 449(5) | 5513(10) | 20(4) |
| C(55) | 7976(10) | 603(5) | 6035(10) | 20(4) |
| C(56) | 8427(13) | 782(6) | 6964(12) | 39(5) |
| C(57) | 7682(14) | 972(6) | 7319(14) | 55(6) |
| C(58) | 8993(14) | 485(6) | 7599(14) | 57(6) |
| C(59) | 9482(11) | 1131(5) | 4086(10) | 25(4) |
| C(60) | 8434(11) | 1215(5) | 2596(11) | 24(4) |
| C(61) | 8135(9) | 1054(4) | 1655(7) | 36(5) |

TABLE 4-continued

Atomic Coordinates and Their Estimated Standard Deviations for Ixazomib Pattern F

| | x | y | z | U(eq) |
|---|---|---|---|---|
| C(62) | 8400(8) | 1229(3) | 971(10) | 63(7) |
| C(63) | 8115(10) | 1058(4) | 122(8) | 79(8) |
| C(64) | 7566(10) | 712(4) | −43(7) | 78(8) |
| C(65) | 7301(9) | 537(3) | 640(9) | 57(6) |
| C(66) | 7586(9) | 708(4) | 1489(8) | 45(5) |
| C(67) | 7848(10) | −1147(5) | 4633(11) | 23(4) |
| C(68) | 8042(11) | −810(4) | 3413(10) | 19(4) |
| C(69) | 7506(11) | −825(5) | 2443(10) | 26(4) |
| C(70) | 8116(13) | −953(6) | 1811(13) | 51(6) |
| C(71) | 8702(14) | −615(6) | 1705(14) | 48(6) |
| C(72) | 7453(14) | −1103(7) | 915(14) | 67(7) |
| C(73) | 7777(11) | −1502(5) | 5241(11) | 22(4) |
| C(74) | 8539(12) | −1202(5) | 6677(11) | 29(4) |
| C(75) | 8426(12) | −1012(5) | 7511(12) | 33(4) |
| C(76) | 8950(13) | −1120(6) | 8360(14) | 51(6) |
| C(77) | 8861(13) | −917(6) | 9117(14) | 49(6) |
| C(78) | 8176(13) | −616(6) | 8962(14) | 46(6) |
| C(79) | 7641(12) | −505(5) | 8122(12) | 32(5) |
| C(80) | 7748(11) | −709(5) | 7397(11) | 27(4) |
| C(81) | 5034(11) | 720(5) | 7821(12) | 32(5) |
| C(82) | 4884(12) | 662(6) | 8669(12) | 36(5) |
| C(83) | 4560(11) | 304(5) | 8858(12) | 32(4) |
| C(84) | 4287(12) | 17(6) | 8206(12) | 37(5) |
| C(85) | 4541(13) | 3407(6) | 7525(13) | 44(5) |
| C(86) | 4906(12) | 3762(5) | 7323(12) | 31(4) |
| C(87) | 5071(11) | 3820(5) | 6431(11) | 24(4) |
| C(88) | 4755(12) | 4224(5) | 5069(11) | 28(4) |
| C(89) | 4717(11) | 3863(5) | 4446(11) | 27(4) |
| C(90) | 5513(10) | 3476(4) | 3549(10) | 16(4) |
| C(91) | 5252(10) | 3627(5) | 2565(10) | 22(4) |
| C(92) | 4282(10) | 3784(5) | 2142(10) | 20(4) |
| C(93) | 3565(11) | 3461(5) | 2032(11) | 30(4) |
| C(94) | 4216(12) | 3974(5) | 1248(12) | 35(4) |
| C(95) | 7863(10) | 2188(5) | 4795(10) | 21(4) |
| C(96) | 8043(11) | 2494(4) | 3523(10) | 19(4) |
| C(100) | 6870(16) | 2883(7) | 1120(16) | 89(8) |
| C(101) | 7789(10) | 1857(4) | 5439(10) | 21(4) |
| C(102) | 8570(12) | 2153(5) | 6880(11) | 26(4) |
| C(103) | 8488(11) | 2353(5) | 7719(11) | 28(4) |
| C(104) | 9043(12) | 2219(5) | 8574(12) | 34(5) |
| C(105) | 8950(13) | 2429(6) | 9327(14) | 46(6) |
| C(106) | 8309(13) | 2734(6) | 9217(14) | 48(6) |
| C(107) | 7779(13) | 2852(5) | 8368(13) | 37(5) |
| C(108) | 7844(11) | 2666(5) | 7618(12) | 28(4) |
| C(109) | 9075(10) | 4142(5) | 4489(10) | 20(4) |
| C(110) | 8591(10) | 3797(4) | 5520(10) | 14(3) |
| C(111) | 7938(10) | 3967(5) | 5984(10) | 20(4) |
| C(112) | 8347(11) | 4175(5) | 6871(11) | 26(4) |
| C(113) | 7595(13) | 4358(5) | 7198(13) | 43(5) |
| C(114) | 8924(13) | 3902(6) | 7569(14) | 50(6) |
| C(115) | 9586(11) | 4444(4) | 4111(10) | 18(4) |
| C(116) | 8588(11) | 4543(4) | 2601(10) | 19(4) |
| C(117) | 8419(8) | 4424(4) | 1628(6) | 28(4) |
| C(118) | 7745(8) | 4140(4) | 1231(8) | 45(5) |
| C(119) | 7577(8) | 4033(4) | 341(8) | 67(7) |
| C(120) | 8083(9) | 4211(4) | −152(6) | 64(7) |
| C(121) | 8756(9) | 4495(4) | 245(8) | 56(6) |
| C(122) | 8924(7) | 4602(3) | 1135(8) | 57(6) |
| C(123) | 5151(12) | 4079(6) | 7918(12) | 39(5) |
| C(124) | 5055(12) | 4018(5) | 8780(12) | 33(5) |
| C(125) | 4750(13) | 3675(6) | 9013(15) | 54(6) |
| C(126) | 4456(12) | 3373(6) | 8376(11) | 48(6) |
| B(1) | 3451(12) | 1702(5) | 6253(12) | 18(4) |
| B(2) | 1851(12) | 1925(5) | 5520(11) | 13(4) |
| B(3) | 2218(12) | 1188(5) | 5958(11) | 13(4) |
| B(4) | 6541(12) | 36(5) | 3822(12) | 14(4) |
| B(5) | 8112(12) | 248(5) | 4545(12) | 14(4) |
| B(6) | 7730(12) | −481(5) | 4052(12) | 15(4) |
| B(7) | 6537(13) | 3360(6) | 3894(12) | 21(5) |
| B(8) | 7778(12) | 2850(5) | 4158(12) | 17(4) |
| B(9) | 8128(12) | 3583(5) | 4550(11) | 14(4) |
| C(99) | 8594(16) | 2755(8) | 1839(17) | 75(8) |
| C(98) | 7690(14) | 2831(7) | 2026(15) | 65(7) |
| C(97) | 7471(12) | 2487(5) | 2561(11) | 29(4) |
| O(30) | −81(8) | 3145(4) | 3961(8) | 43(3) |
| H(1) | 5898 | 2561 | 4137 | 31 |
| H(2) | 4188 | 2336 | 5878 | 14 |
| H(3) | 538 | 2640 | 4333 | 24 |
| H(4) | 208 | 2662 | 7133 | 19 |
| H(5) | 1935 | 226 | 6311 | 22 |
| H(6) | 2640 | 321 | 3704 | 28 |
| H(7) | 4034 | 899 | 5916 | 25 |
| H(8) | 5796 | 669 | 4215 | 15 |
| H(9) | 9443 | 973 | 5708 | 20 |
| H(10) | 9653 | 1000 | 2874 | 23 |
| H(11) | 8028 | −1434 | 3656 | 26 |
| H(12) | 7311 | −1392 | 6257 | 31 |
| H(13) | 4124 | 4232 | 6032 | 34 |
| H(14) | 5823 | 4002 | 4245 | 18 |
| H(15) | 7952 | 1876 | 3805 | 23 |
| H(16) | 7331 | 1988 | 6449 | 28 |
| H(17) | 9473 | 4304 | 5720 | 17 |
| H(18) | 9773 | 4297 | 2902 | 24 |
| H(4A) | 4641 | 2680 | 4903 | 31 |
| H(4B) | 5699 | 2766 | 5387 | 31 |
| H(6) | 4882 | 1578 | 6518 | 25 |
| H(7A) | 4341 | 2178 | 7610 | 23 |
| H(7B) | 4645 | 1722 | 7922 | 23 |
| H(8) | 5878 | 2321 | 7615 | 30 |
| H(9A) | 7055 | 1881 | 8426 | 46 |
| H(9B) | 6443 | 1676 | 7515 | 46 |
| H(9C) | 6311 | 1544 | 8444 | 46 |
| H(10A) | 5731 | 2075 | 9302 | 72 |
| H(10B) | 5417 | 2510 | 8845 | 72 |
| H(10C) | 6474 | 2390 | 9173 | 72 |
| H(12) | 965 | 1924 | 4166 | 16 |
| H(13A) | 2471 | 2471 | 4429 | 23 |
| H(13B) | 2388 | 2040 | 3944 | 23 |
| H(14) | 1261 | 2721 | 3236 | 38 |
| H(15A) | 2785 | 2832 | 3229 | 67 |
| H(15B) | 2080 | 2822 | 2239 | 67 |
| H(15C) | 2711 | 2433 | 2622 | 67 |
| H(16A) | 802 | 2349 | 1891 | 84 |
| H(16B) | 467 | 2151 | 2662 | 84 |
| H(16C) | 1315 | 1957 | 2425 | 84 |
| H(17A) | 596 | 3074 | 5805 | 25 |
| H(17B) | −240 | 2764 | 5648 | 25 |
| H(21) | 1308 | 2730 | 10306 | 78 |
| H(22) | 2334 | 2182 | 10597 | 87 |
| H(24) | 2525 | 2280 | 8100 | 49 |
| H(26) | 1238 | 894 | 6495 | 22 |
| H(27A) | 2684 | 1098 | 7769 | 32 |
| H(27B) | 2893 | 624 | 7679 | 32 |
| H(28) | 1321 | 483 | 7832 | 66 |
| H(29A) | 675 | 964 | 8474 | 75 |
| H(29B) | 859 | 1179 | 7635 | 75 |
| H(29C) | 1523 | 1267 | 8623 | 75 |
| H(30A) | 2719 | 769 | 9370 | 107 |
| H(30B) | 2675 | 319 | 8961 | 107 |
| H(30C) | 1918 | 464 | 9395 | 107 |
| H(31A) | 2759 | 40 | 5003 | 37 |
| H(31B) | 1672 | −5 | 4668 | 37 |
| H(35) | 438 | 831 | 336 | 70 |
| H(36) | 1677 | 1272 | 516 | 66 |
| H(38) | 2618 | 1024 | 3140 | 30 |
| H(39) | 4479 | 2620 | 2317 | 43 |
| H(41) | 5408 | 1933 | 605 | 41 |
| H(42) | 6038 | 1478 | 1759 | 48 |
| H(46A) | 5324 | 1003 | 5158 | 25 |
| H(46B) | 4273 | 1102 | 4662 | 25 |
| H(48) | 5075 | −74 | 3518 | 23 |
| H(49A) | 5675 | 540 | 2480 | 21 |
| H(49B) | 5351 | 90 | 2127 | 21 |
| H(50) | 4164 | 684 | 2481 | 27 |
| H(51A) | 2962 | 276 | 1578 | 43 |
| H(51B) | 3515 | 65 | 2505 | 43 |
| H(51C) | 3692 | −74 | 1601 | 43 |
| H(52A) | 4322 | 494 | 785 | 53 |
| H(52B) | 4711 | 900 | 1339 | 53 |
| H(52C) | 3635 | 822 | 974 | 53 |

TABLE 4-continued

Atomic Coordinates and Their Estimated Standard Deviations for Ixazomib Pattern F

| | x | y | z | U(eq) |
|---|---|---|---|---|
| H(54) | 9045 | 248 | 5890 | 24 |
| H(55A) | 7569 | 814 | 5669 | 23 |
| H(55B) | 7587 | 372 | 6097 | 23 |
| H(56) | 8835 | 1009 | 6899 | 47 |
| H(57A) | 7280 | 1147 | 6857 | 82 |
| H(57B) | 7974 | 1135 | 7853 | 82 |
| H(57C) | 7323 | 752 | 7469 | 82 |
| H(58A) | 9258 | 617 | 8181 | 86 |
| H(58B) | 9482 | 388 | 7378 | 86 |
| H(58C) | 8615 | 254 | 7661 | 86 |
| H(59A) | 9308 | 1406 | 4239 | 30 |
| H(59B) | 10150 | 1102 | 4360 | 30 |
| H(63) | 8296 | 1177 | −345 | 95 |
| H(64) | 7371 | 594 | −624 | 94 |
| H(66) | 7405 | 589 | 1957 | 53 |
| H(68) | 8696 | −760 | 3470 | 23 |
| H(69A) | 7233 | −553 | 2255 | 31 |
| H(69B) | 7002 | −1024 | 2354 | 31 |
| H(70) | 8516 | −1188 | 2100 | 61 |
| H(71A) | 9107 | −712 | 1377 | 73 |
| H(71B) | 9069 | −516 | 2295 | 73 |
| H(71C) | 8322 | −392 | 1373 | 73 |
| H(72A) | 6917 | −924 | 736 | 100 |
| H(72B) | 7262 | −1383 | 982 | 100 |
| H(72C) | 7760 | −1096 | 457 | 100 |
| H(73A) | 7199 | −1651 | 4966 | 26 |
| H(73B) | 8286 | −1695 | 5298 | 26 |
| H(77) | 9243 | −981 | 9702 | 59 |
| H(78) | 8081 | −483 | 9462 | 55 |
| H(80) | 7361 | −645 | 6814 | 33 |
| H(81) | 5314 | 963 | 7706 | 39 |
| H(83) | 4521 | 253 | 9438 | 38 |
| H(84) | 4020 | −228 | 8330 | 44 |
| H(88A) | 5367 | 4350 | 5225 | 34 |
| H(88B) | 4305 | 4432 | 4749 | 34 |
| H(90) | 5127 | 3238 | 3599 | 20 |
| H(91A) | 5679 | 3848 | 2536 | 26 |
| H(91B) | 5351 | 3398 | 2195 | 26 |
| H(92) | 4169 | 4004 | 2536 | 24 |
| H(93A) | 2969 | 3573 | 1688 | 45 |
| H(93B) | 3548 | 3374 | 2621 | 45 |
| H(93C) | 3708 | 3226 | 1714 | 45 |
| H(94A) | 4272 | 3760 | 834 | 53 |
| H(94B) | 4706 | 4174 | 1325 | 53 |
| H(94C) | 3625 | 4111 | 1006 | 53 |
| H(96) | 8697 | 2527 | 3559 | 23 |
| H(10D) | 6866 | 2651 | 724 | 133 |
| H(10E) | 6949 | 3138 | 826 | 133 |
| H(10F) | 6292 | 2891 | 1253 | 133 |
| H(10G) | 7205 | 1710 | 5180 | 26 |
| H(10H) | 8288 | 1657 | 5504 | 26 |
| H(105) | 9331 | 2360 | 9909 | 55 |
| H(106) | 8230 | 2865 | 9726 | 58 |
| H(108) | 7465 | 2747 | 7043 | 33 |
| H(110) | 9009 | 3596 | 5927 | 16 |
| H(11A) | 7529 | 4165 | 5575 | 24 |
| H(11B) | 7553 | 3739 | 6072 | 24 |
| H(112) | 8738 | 4405 | 6784 | 31 |
| H(11A) | 7185 | 4523 | 6722 | 65 |
| H(11B) | 7870 | 4531 | 7721 | 65 |
| H(11C) | 7249 | 4137 | 7360 | 65 |
| H(11D) | 8553 | 3676 | 7674 | 75 |
| H(11E) | 9182 | 4056 | 8124 | 75 |
| H(11F) | 9419 | 3792 | 7372 | 75 |
| H(11G) | 9435 | 4724 | 4256 | 21 |
| H(11H) | 10248 | 4403 | 4399 | 21 |
| H(119) | 7117 | 3839 | 70 | 80 |
| H(120) | 7968 | 4138 | −760 | 76 |
| H(122) | 9384 | 4796 | 1407 | 69 |
| H(123) | 5376 | 4329 | 7763 | 47 |
| H(125) | 4732 | 3636 | 9605 | 64 |
| H(126) | 4186 | 3133 | 8523 | 57 |
| H(99A) | 9104 | 2818 | 2376 | 113 |
| H(99B) | 8627 | 2931 | 1347 | 113 |
| H(99C) | 8629 | 2468 | 1674 | 113 |
| H(98) | 7747 | 3089 | 2379 | 78 |
| H(97A) | 6821 | 2505 | 2524 | 35 |
| H(97B) | 7564 | 2223 | 2295 | 35 |

$U_{eq} = (1/3)\Sigma_i\Sigma_j U_{ij} a^*_i a^*_j \cdot a_i \cdot a_j$

Hydrogen atoms are included in calculation of structure factors but not refined

TABLE 5

Table of Bond Distances in Ångstroms for Ixazomib Pattern F

| Cl(1)—C(1) | 1.729(17) |
|---|---|
| Cl(2)—C(20) | 1.692(11) |
| Cl(3)—C(23) | 1.739(10) |
| Cl(4)—C(34) | 1.74(2) |
| Cl(5)—C(37) | 1.727(18) |
| Cl(6)—C(40) | 1.721(18) |
| Cl(7)—C(43) | 1.716(17) |
| Cl(8)—C(62) | 1.679(11) |
| Cl(9)—C(65) | 1.738(11) |
| Cl(10)—C(76) | 1.73(2) |
| Cl(11)—C(79) | 1.707(18) |
| Cl(12)—C(82) | 1.746(19) |
| Cl(13)—C(85) | 1.71(2) |
| Cl(14)—C(104) | 1.692(18) |
| Cl(15)—C(107) | 1.745(19) |
| Cl(16)—C(118) | 1.679(10) |
| Cl(17)—C(121) | 1.730(10) |
| Cl(18)—C(124) | 1.747(18) |
| O(1)—C(3) | 1.257(19) |
| O(2)—C(5) | 1.264(18) |
| O(3)—B(1) | 1.35(2) |
| O(3)—B(2) | 1.484(19) |
| O(4)—C(11) | 1.294(17) |
| O(4)—B(2) | 1.59(2) |
| O(5)—C(18) | 1.212(17) |
| O(6)—B(2) | 1.405(18) |
| O(6)—B(3) | 1.424(19) |
| O(7)—C(25) | 1.264(17) |
| O(7)—B(3) | 1.626(19) |
| O(8)—C(32) | 1.248(18) |
| O(9)—B(1) | 1.368(19) |
| O(9)—B(3) | 1.466(19) |
| O(10)—C(45) | 1.246(19) |
| O(11)—C(47) | 1.237(17) |
| O(12)—B(4) | 1.322(19) |
| O(12)—B(5) | 1.46(2) |
| O(13)—C(53) | 1.270(17) |
| O(13)—B(5) | 1.62(2) |
| O(14)—C(60) | 1.206(18) |
| O(15)—B(6) | 1.411(19) |
| O(15)—B(5) | 1.428(19) |
| O(16)—C(67) | 1.260(17) |
| O(16)—B(6) | 1.63(2) |
| O(17)—C(74) | 1.233(19) |
| O(18)—B(4) | 1.356(19) |
| O(18)—B(6) | 1.47(2) |
| O(19)—C(87) | 1.242(18) |
| O(20)—C(89) | 1.270(18) |
| O(21)—B(7) | 1.38(2) |
| O(21)—B(8) | 1.47(2) |
| O(22)—C(95) | 1.268(17) |
| O(22)—B(8) | 1.66(2) |
| O(23)—C(102) | 1.259(19) |
| O(24)—B(8) | 1.39(2) |
| O(24)—B(9) | 1.422(18) |
| O(25)—C(109) | 1.296(17) |
| O(25)—B(9) | 1.63(2) |
| O(26)—C(116) | 1.220(17) |
| O(27)—B(7) | 1.34(2) |
| O(27)—B(9) | 1.45(2) |
| N(1)—C(3) | 1.34(2) |
| N(1)—C(4) | 1.43(2) |

TABLE 5-continued

Table of Bond Distances in Ångstroms for Ixazomib Pattern F

| | |
|---|---|
| N(1)—H(1) | 0.8800 |
| N(2)—C(5) | 1.293(19) |
| N(2)—C(6) | 1.443(18) |
| N(2)—H(2) | 0.8800 |
| N(3)—C(11) | 1.280(19) |
| N(3)—C(12) | 1.474(18) |
| N(3)—H(3) | 0.8800 |
| N(4)—C(18) | 1.346(19) |
| N(4)—C(17) | 1.458(18) |
| N(4)—H(4) | 0.8800 |
| N(5)—C(25) | 1.260(18) |
| N(5)—C(26) | 1.468(18) |
| N(5)—H(5) | 0.8800 |
| N(6)—C(32) | 1.311(19) |
| N(6)—C(31) | 1.43(2) |
| N(6)—H(6) | 0.8800 |
| N(7)—C(45) | 1.332(19) |
| N(7)—C(46) | 1.45(2) |
| N(7)—H(7) | 0.8800 |
| N(8)—C(47) | 1.343(19) |
| N(8)—C(48) | 1.427(18) |
| N(8)—H(8) | 0.8800 |
| N(9)—C(53) | 1.287(18) |
| N(9)—C(54) | 1.483(18) |
| N(9)—H(9) | 0.8800 |
| N(10)—C(60) | 1.329(18) |
| N(10)—C(59) | 1.466(19) |
| N(10)—H(10) | 0.8800 |
| N(11)—C(67) | 1.273(19) |
| N(11)—C(68) | 1.469(19) |
| N(11)—H(11) | 0.8800 |
| N(12)—C(74) | 1.33(2) |
| N(12)—C(73) | 1.409(19) |
| N(12)—H(12) | 0.8800 |
| N(13)—C(87) | 1.35(2) |
| N(13)—C(88) | 1.46(2) |
| N(13)—H(13) | 0.8800 |
| N(14)—C(89) | 1.323(19) |
| N(14)—C(90) | 1.460(18) |
| N(14)—H(14) | 0.8800 |
| N(15)—C(95) | 1.283(19) |
| N(15)—C(96) | 1.478(19) |
| N(15)—H(15) | 0.8800 |
| N(16)—C(102) | 1.320(19) |
| N(16)—C(101) | 1.411(19) |
| N(16)—H(16) | 0.8800 |
| N(17)—C(109) | 1.280(19) |
| N(17)—C(110) | 1.482(18) |
| N(17)—H(17) | 0.8800 |
| N(18)—C(116) | 1.317(18) |
| N(18)—C(115) | 1.483(18) |
| N(18)—H(18) | 0.8800 |
| C(1)—C(2) | 1.37(2) |
| C(1)—C(42) | 1.40(2) |
| C(2)—C(39) | 1.40(2) |
| C(2)—C(3) | 1.50(2) |
| C(4)—C(5) | 1.51(2) |
| C(4)—H(4A) | 0.9900 |
| C(4)—H(4B) | 0.9900 |
| C(6)—C(7) | 1.55(2) |
| C(6)—B(1) | 1.59(2) |
| C(6)—H(6) | 1.0000 |
| C(7)—C(8) | 1.55(2) |
| C(7)—H(7A) | 0.9900 |
| C(7)—H(7B) | 0.9900 |
| C(8)—C(9) | 1.50(2) |
| C(8)—C(10) | 1.52(2) |
| C(8)—H(8) | 1.0000 |
| C(9)—H(9A) | 0.9800 |
| C(9)—H(9B) | 0.9800 |
| C(9)—H(9C) | 0.9800 |
| C(10)—H(10A) | 0.9800 |
| C(10)—H(10B) | 0.9800 |
| C(10)—H(10C) | 0.9800 |
| C(11)—C(17) | 1.52(2) |
| C(12)—C(13) | 1.53(2) |
| C(12)—B(2) | 1.61(2) |
| C(12)—H(12) | 1.0000 |
| C(13)—C(14) | 1.51(2) |
| C(13)—H(13A) | 0.9900 |
| C(13)—H(13B) | 0.9900 |
| C(14)—C(16) | 1.49(3) |
| C(14)—C(15) | 1.54(3) |
| C(14)—H(14) | 1.0000 |
| C(15)—H(15A) | 0.9800 |
| C(15)—H(15B) | 0.9800 |
| C(15)—H(15C) | 0.9800 |
| C(16)—H(16A) | 0.9800 |
| C(16)—H(16B) | 0.9800 |
| C(16)—H(16C) | 0.9800 |
| C(17)—H(17A) | 0.9900 |
| C(17)—H(17B) | 0.9900 |
| C(18)—C(19) | 1.516(18) |
| C(19)—C(20) | 1.3900 |
| C(19)—C(24) | 1.3900 |
| C(20)—C(21) | 1.3900 |
| C(21)—C(22) | 1.3900 |
| C(21)—H(21) | 0.9500 |
| C(22)—C(23) | 1.3900 |
| C(22)—H(22) | 0.9500 |
| C(23)—C(24) | 1.3900 |
| C(24)—H(24) | 0.9500 |
| C(25)—C(31) | 1.51(2) |
| C(26)—C(27) | 1.51(2) |
| C(26)—B(3) | 1.65(2) |
| C(26)—H(26) | 1.0000 |
| C(27)—C(28) | 1.63(3) |
| C(27)—H(27A) | 0.9900 |
| C(27)—H(27B) | 0.9900 |
| C(28)—C(29) | 1.48(3) |
| C(28)—C(30) | 1.52(3) |
| C(28)—H(28) | 1.0000 |
| C(29)—H(29A) | 0.9800 |
| C(29)—H(29B) | 0.9800 |
| C(29)—H(29C) | 0.9800 |
| C(30)—H(30A) | 0.9800 |
| C(30)—H(30B) | 0.9800 |
| C(30)—H(30C) | 0.9800 |
| C(31)—H(31A) | 0.9900 |
| C(31)—H(31B) | 0.9900 |
| C(32)—C(33) | 1.52(2) |
| C(33)—C(38) | 1.36(2) |
| C(33)—C(34) | 1.40(2) |
| C(34)—C(35) | 1.41(3) |
| C(35)—C(36) | 1.38(3) |
| C(35)—H(35) | 0.9500 |
| C(36)—C(37) | 1.43(3) |
| C(36)—H(36) | 0.9500 |
| C(37)—C(38) | 1.33(2) |
| C(38)—H(38) | 0.9500 |
| C(39)—C(40) | 1.45(2) |
| C(39)—H(39) | 0.9500 |
| C(40)—C(41) | 1.37(2) |
| C(41)—C(42) | 1.37(2) |
| C(41)—H(41) | 0.9500 |
| C(42)—H(42) | 0.9500 |
| C(43)—C(44) | 1.37(2) |
| C(43)—C(84) | 1.39(2) |
| C(44)—C(81) | 1.37(2) |
| C(44)—C(45) | 1.51(2) |
| C(46)—C(47) | 1.48(2) |
| C(46)—H(46A) | 0.9900 |
| C(46)—H(46B) | 0.9900 |
| C(48)—C(49) | 1.57(2) |
| C(48)—B(4) | 1.63(2) |
| C(48)—H(48) | 1.0000 |
| C(49)—C(50) | 1.52(2) |
| C(49)—H(49A) | 0.9900 |
| C(49)—H(49B) | 0.9900 |
| C(50)—C(52) | 1.50(2) |
| C(50)—C(51) | 1.50(2) |
| C(50)—H(50) | 1.0000 |
| C(51)—H(51A) | 0.9800 |
| C(51)—H(51B) | 0.9800 |
| C(51)—H(51C) | 0.9800 |
| C(52)—H(52A) | 0.9800 |

TABLE 5-continued

Table of Bond Distances in Ångstroms for Ixazomib Pattern F

| | |
|---|---|
| C(52)—H(52B) | 0.9800 |
| C(52)—H(52C) | 0.9800 |
| C(53)—C(59) | 1.50(2) |
| C(54)—C(55) | 1.54(2) |
| C(54)—B(5) | 1.62(2) |
| C(54)—H(54) | 1.0000 |
| C(55)—C(56) | 1.53(2) |
| C(55)—H(55A) | 0.9900 |
| C(55)—H(55B) | 0.9900 |
| C(56)—C(58) | 1.47(3) |
| C(56)—C(57) | 1.56(3) |
| C(56)—H(56) | 1.0000 |
| C(57)—H(57A) | 0.9800 |
| C(57)—H(57B) | 0.9800 |
| C(57)—H(57C) | 0.9800 |
| C(58)—H(58A) | 0.9800 |
| C(58)—H(58B) | 0.9800 |
| C(58)—H(58C) | 0.9800 |
| C(59)—H(59A) | 0.9900 |
| C(59)—H(59B) | 0.9900 |
| C(60)—C(61) | 1.505(18) |
| C(61)—C(62) | 1.3900 |
| C(61)—C(66) | 1.3900 |
| C(62)—C(63) | 1.3900 |
| C(63)—C(64) | 1.3900 |
| C(63)—H(63) | 0.9500 |
| C(64)—C(65) | 1.3900 |
| C(64)—H(64) | 0.9500 |
| C(65)—C(66) | 1.3900 |
| C(66)—H(66) | 0.9500 |
| C(67)—C(73) | 1.53(2) |
| C(68)—C(69) | 1.49(2) |
| C(68)—B(6) | 1.65(2) |
| C(68)—H(68) | 1.0000 |
| C(69)—C(70) | 1.63(2) |
| C(69)—H(69A) | 0.9900 |
| C(69)—H(69B) | 0.9900 |
| C(70)—C(71) | 1.47(3) |
| C(70)—C(72) | 1.54(3) |
| C(70)—H(70) | 1.0000 |
| C(71)—H(71A) | 0.9800 |
| C(71)—H(71B) | 0.9800 |
| C(71)—H(71C) | 0.9800 |
| C(72)—H(72A) | 0.9800 |
| C(72)—H(72B) | 0.9800 |
| C(72)—H(72C) | 0.9800 |
| C(73)—H(73A) | 0.9900 |
| C(73)—H(73B) | 0.9900 |
| C(74)—C(75) | 1.51(2) |
| C(75)—C(76) | 1.38(2) |
| C(75)—C(80) | 1.41(2) |
| C(76)—C(77) | 1.41(3) |
| C(77)—C(78) | 1.41(3) |
| C(77)—H(77) | 0.9500 |
| C(78)—C(79) | 1.37(2) |
| C(78)—H(78) | 0.9500 |
| C(79)—C(80) | 1.38(2) |
| C(80)—H(80) | 0.9500 |
| C(81)—C(82) | 1.44(2) |
| C(81)—H(81) | 0.9500 |
| C(82)—C(83) | 1.34(2) |
| C(83)—C(84) | 1.36(2) |
| C(83)—H(83) | 0.9500 |
| C(84)—H(84) | 0.9500 |
| C(85)—C(86) | 1.37(2) |
| C(85)—C(126) | 1.39(3) |
| C(86)—C(123) | 1.37(2) |
| C(86)—C(87) | 1.52(2) |
| C(88)—C(89) | 1.52(2) |
| C(88)—H(88A) | 0.9900 |
| C(88)—H(88B) | 0.9900 |
| C(90)—B(7) | 1.55(2) |
| C(90)—C(91) | 1.56(2) |
| C(90)—H(90) | 1.0000 |
| C(91)—C(92) | 1.53(2) |
| C(91)—H(91A) | 0.9900 |
| C(91)—H(91B) | 0.9900 |
| C(92)—C(93) | 1.50(2) |
| C(92)—C(94) | 1.51(2) |
| C(92)—H(92) | 1.0000 |
| C(93)—H(93A) | 0.9800 |
| C(93)—H(93B) | 0.9800 |
| C(93)—H(93C) | 0.9800 |
| C(94)—H(94A) | 0.9800 |
| C(94)—H(94B) | 0.9800 |
| C(94)—H(94C) | 0.9800 |
| C(95)—C(101) | 1.51(2) |
| C(96)—C(97) | 1.50(2) |
| C(96)—B(8) | 1.67(2) |
| C(96)—H(96) | 1.0000 |
| C(100)—C(98) | 1.59(3) |
| C(100)—H(10D) | 0.9800 |
| C(100)—H(10E) | 0.9800 |
| C(100)—H(10F) | 0.9800 |
| C(101)—H(10G) | 0.9900 |
| C(101)—H(10H) | 0.9900 |
| C(102)—C(103) | 1.52(2) |
| C(103)—C(108) | 1.40(2) |
| C(103)—C(104) | 1.42(2) |
| C(104)—C(105) | 1.42(2) |
| C(105)—C(106) | 1.38(3) |
| C(105)—H(105) | 0.9500 |
| C(106)—C(107) | 1.39(3) |
| C(106)—H(106) | 0.9500 |
| C(107)—C(108) | 1.36(2) |
| C(108)—H(108) | 0.9500 |
| C(109)—C(115) | 1.50(2) |
| C(110)—C(111) | 1.53(2) |
| C(110)—B(9) | 1.63(2) |
| C(110)—H(110) | 1.0000 |
| C(111)—C(112) | 1.50(2) |
| C(111)—H(11A) | 0.9900 |
| C(111)—H(11B) | 0.9900 |
| C(112)—C(114) | 1.48(2) |
| C(112)—C(113) | 1.53(2) |
| C(112)—H(112) | 1.0000 |
| C(113)—H(11A) | 0.9800 |
| C(113)—H(11B) | 0.9800 |
| C(113)—H(11C) | 0.9800 |
| C(114)—H(11D) | 0.9800 |
| C(114)—H(11E) | 0.9800 |
| C(114)—H(11F) | 0.9800 |
| C(115)—H(11G) | 0.9900 |
| C(115)—H(11H) | 0.9900 |
| C(116)—C(117) | 1.523(18) |
| C(117)—C(118) | 1.3900 |
| C(117)—C(122) | 1.3900 |
| C(118)—C(119) | 1.3900 |
| C(119)—C(120) | 1.3900 |
| C(119)—H(119) | 0.9500 |
| C(120)—C(121) | 1.3900 |
| C(120)—H(120) | 0.9500 |
| C(121)—C(122) | 1.3900 |
| C(122)—H(122) | 0.9500 |
| C(123)—C(124) | 1.43(2) |
| C(123)—H(123) | 0.9500 |
| C(124)—C(125) | 1.31(3) |
| C(125)—C(126) | 1.38(3) |
| C(125)—H(125) | 0.9500 |
| C(126)—H(126) | 0.9500 |
| C(99)—C(98) | 1.54(3) |
| C(99)—H(99A) | 0.9800 |
| C(99)—H(99B) | 0.9800 |
| C(99)—H(99C) | 0.9800 |
| C(98)—C(97) | 1.51(3) |
| C(98)—H(98) | 1.0000 |
| C(97)—H(97A) | 0.9900 |
| C(97)—H(97B) | 0.9900 |

Numbers in parentheses are estimated standard deviations in the least significant digits.

TABLE 6

| Bond Angles in Degrees for Ixazomib Pattern F | |
|---|---|
| B(1)—O(3)—B(2) | 122.8(12) |
| C(11)—O(4)—B(2) | 106.9(12) |
| B(2)—O(6)—B(3) | 126.3(12) |
| C(25)—O(7)—B(3) | 107.1(11) |
| B(1)—O(9)—B(3) | 121.5(12) |
| B(4)—O(12)—B(5) | 121.9(12) |
| C(53)—O(13)—B(5) | 107.2(12) |
| B(6)—O(15)—B(5) | 125.2(12) |
| C(67)—O(16)—B(6) | 108.1(12) |
| B(4)—O(18)—B(6) | 119.5(12) |
| B(7)—O(21)—B(8) | 120.5(12) |
| C(95)—O(22)—B(8) | 107.5(11) |
| B(8)—O(24)—B(9) | 124.4(12) |
| C(109)—O(25)—B(9) | 107.4(11) |
| B(7)—O(27)—B(9) | 123.5(12) |
| C(3)—N(1)—C(4) | 120.4(14) |
| C(3)—N(1)—H(1) | 119.8 |
| C(4)—N(1)—H(1) | 119.8 |
| C(5)—N(2)—C(6) | 127.3(13) |
| C(5)—N(2)—H(2) | 116.4 |
| C(6)—N(2)—H(2) | 116.4 |
| C(11)—N(3)—C(12) | 111.1(13) |
| C(11)—N(3)—H(3) | 124.5 |
| C(12)—N(3)—H(3) | 124.5 |
| C(18)—N(4)—C(17) | 118.4(13) |
| C(18)—N(4)—H(4) | 120.8 |
| C(17)—N(4)—H(4) | 120.8 |
| C(25)—N(5)—C(26) | 114.1(13) |
| C(25)—N(5)—H(5) | 122.9 |
| C(26)—N(5)—H(5) | 122.9 |
| C(32)—N(6)—C(31) | 121.5(15) |
| C(32)—N(6)—H(6) | 119.3 |
| C(31)—N(6)—H(6) | 119.3 |
| C(45)—N(7)—C(46) | 119.0(14) |
| C(45)—N(7)—H(7) | 120.5 |
| C(46)—N(7)—H(7) | 120.5 |
| C(47)—N(8)—C(48) | 126.7(13) |
| C(47)—N(8)—H(8) | 116.6 |
| C(48)—N(8)—H(8) | 116.6 |
| C(53)—N(9)—C(54) | 110.5(12) |
| C(53)—N(9)—H(9) | 124.8 |
| C(54)—N(9)—H(9) | 124.8 |
| C(60)—N(10)—C(59) | 119.5(14) |
| C(60)—N(10)—H(10) | 120.2 |
| C(59)—N(10)—H(10) | 120.2 |
| C(67)—N(11)—C(68) | 115.1(13) |
| C(67)—N(11)—H(11) | 122.5 |
| C(68)—N(11)—H(11) | 122.5 |
| C(74)—N(12)—C(73) | 123.5(15) |
| C(74)—N(12)—H(12) | 118.3 |
| C(73)—N(12)—H(12) | 118.3 |
| C(87)—N(13)—C(88) | 120.3(14) |
| C(87)—N(13)—H(13) | 119.8 |
| C(88)—N(13)—H(13) | 119.8 |
| C(89)—N(14)—C(90) | 127.0(13) |
| C(89)—N(14)—H(14) | 116.5 |
| C(90)—N(14)—H(14) | 116.5 |
| C(95)—N(15)—C(96) | 115.3(13) |
| C(95)—N(15)—H(15) | 122.4 |
| C(96)—N(15)—H(15) | 122.4 |
| C(102)—N(16)—C(101) | 124.4(14) |
| C(102)—N(16)—H(16) | 117.8 |
| C(101)—N(16)—H(16) | 117.8 |
| C(109)—N(17)—C(110) | 111.7(12) |
| C(109)—N(17)—H(17) | 124.1 |
| C(110)—N(17)—H(17) | 124.1 |
| C(116)—N(18)—C(115) | 119.4(13) |
| C(116)—N(18)—H(18) | 120.3 |
| C(115)—N(18)—H(18) | 120.3 |
| C(2)—C(1)—C(42) | 119.8(16) |
| C(2)—C(1)—Cl(1) | 121.2(13) |
| C(42)—C(1)—Cl(1) | 118.7(13) |
| C(1)—C(2)—C(39) | 120.5(16) |
| C(1)—C(2)—C(3) | 122.1(15) |
| C(39)—C(2)—C(3) | 117.4(15) |
| O(1)—C(3)—N(1) | 121.1(16) |
| O(1)—C(3)—C(2) | 121.5(15) |
| N(1)—C(3)—C(2) | 117.4(15) |
| N(1)—C(4)—C(5) | 114.0(13) |
| N(1)—C(4)—H(4A) | 108.8 |
| C(5)—C(4)—H(4A) | 108.8 |
| N(1)—C(4)—H(4B) | 108.8 |
| C(5)—C(4)—H(4B) | 108.8 |
| H(4A)—C(4)—H(4B) | 107.7 |
| O(2)—C(5)—N(2) | 120.3(14) |
| O(2)—C(5)—C(4) | 120.2(15) |
| N(2)—C(5)—C(4) | 119.5(14) |
| N(2)—C(6)—C(7) | 111.0(12) |
| N(2)—C(6)—B(1) | 107.1(12) |
| C(7)—C(6)—B(1) | 107.4(13) |
| N(2)—C(6)—H(6) | 110.4 |
| C(7)—C(6)—H(6) | 110.4 |
| B(1)—C(6)—H(6) | 110.4 |
| C(8)—C(7)—C(6) | 115.7(13) |
| C(8)—C(7)—H(7A) | 108.4 |
| C(6)—C(7)—H(7A) | 108.4 |
| C(8)—C(7)—H(7B) | 108.4 |
| C(6)—C(7)—H(7B) | 108.4 |
| H(7A)—C(7)—H(7B) | 107.4 |
| C(9)—C(8)—C(10) | 109.0(14) |
| C(9)—C(8)—C(7) | 114.0(13) |
| C(10)—C(8)—C(7) | 109.5(14) |
| C(9)—C(8)—H(8) | 108.1 |
| C(10)—C(8)—H(8) | 108.1 |
| C(7)—C(8)—H(8) | 108.1 |
| C(8)—C(9)—H(9A) | 109.5 |
| C(8)—C(9)—H(9B) | 109.5 |
| H(9A)—C(9)—H(9B) | 109.5 |
| C(8)—C(9)—H(9C) | 109.5 |
| H(9A)—C(9)—H(9C) | 109.5 |
| H(9B)—C(9)—H(9C) | 109.5 |
| C(8)—C(10)—H(10A) | 109.5 |
| C(8)—C(10)—H(10B) | 109.5 |
| H(10A)—C(10)—H(10B) | 109.5 |
| C(8)—C(10)—H(10C) | 109.5 |
| H(10A)—C(10)—H(10C) | 109.5 |
| H(10B)—C(10)—H(10C) | 109.5 |
| N(3)—C(11)—O(4) | 119.2(14) |
| N(3)—C(11)—C(17) | 122.2(14) |
| O(4)—C(11)—C(17) | 118.6(14) |
| N(3)—C(12)—C(13) | 110.8(12) |
| N(3)—C(12)—B(2) | 102.9(12) |
| C(13)—C(12)—B(2) | 118.3(12) |
| N(3)—C(12)—H(12) | 108.1 |
| C(13)—C(12)—H(12) | 108.1 |
| B(2)—C(12)—H(12) | 108.1 |
| C(14)—C(13)—C(12) | 119.4(13) |
| C(14)—C(13)—H(13A) | 107.5 |
| C(12)—C(13)—H(13A) | 107.5 |
| C(14)—C(13)—H(13B) | 107.5 |
| C(12)—C(13)—H(13B) | 107.5 |
| H(13A)—C(13)—H(13B) | 107.0 |
| C(16)—C(14)—C(13) | 112.4(15) |
| C(16)—C(14)—C(15) | 110.7(16) |
| C(13)—C(14)—C(15) | 112.2(14) |
| C(16)—C(14)—H(14) | 107.1 |
| C(13)—C(14)—H(14) | 107.1 |
| C(15)—C(14)—H(14) | 107.1 |
| C(14)—C(15)—H(15A) | 109.5 |
| C(14)—C(15)—H(15B) | 109.5 |
| H(15A)—C(15)—H(15B) | 109.5 |
| C(14)—C(15)—H(15C) | 109.5 |
| H(15A)—C(15)—H(15C) | 109.5 |
| H(15B)—C(15)—H(15C) | 109.5 |
| C(14)—C(16)—H(16A) | 109.5 |
| C(14)—C(16)—H(16B) | 109.5 |
| H(16A)—C(16)—H(16B) | 109.5 |
| C(14)—C(16)—H(16C) | 109.5 |
| H(16A)—C(16)—H(16C) | 109.5 |
| H(16B)—C(16)—H(16C) | 109.5 |
| N(4)—C(17)—C(11) | 112.4(12) |
| N(4)—C(17)—H(17A) | 109.1 |
| C(11)—C(17)—H(17A) | 109.1 |
| N(4)—C(17)—H(17B) | 109.1 |
| C(11)—C(17)—H(17B) | 109.1 |
| H(17A)—C(17)—H(17B) | 107.9 |

TABLE 6-continued

Bond Angles in Degrees for Ixazomib Pattern F

| | |
|---|---|
| O(5)—C(18)—N(4) | 124.0(15) |
| O(5)—C(18)—C(19) | 123.4(14) |
| N(4)—C(18)—C(19) | 112.6(13) |
| C(20)—C(19)—C(24) | 120.0 |
| C(20)—C(19)—C(18) | 126.0(10) |
| C(24)—C(19)—C(18) | 114.0(10) |
| C(19)—C(20)—C(21) | 120.0 |
| C(19)—C(20)—Cl(2) | 120.7(8) |
| C(21)—C(20)—Cl(2) | 119.3(8) |
| C(20)—C(21)—C(22) | 120.0 |
| C(20)—C(21)—H(21) | 120.0 |
| C(22)—C(21)—H(21) | 120.0 |
| C(23)—C(22)—C(21) | 120.0 |
| C(23)—C(22)—H(22) | 120.0 |
| C(21)—C(22)—H(22) | 120.0 |
| C(24)—C(23)—C(22) | 120.0 |
| C(24)—C(23)—Cl(3) | 119.7(8) |
| C(22)—C(23)—Cl(3) | 120.2(8) |
| C(23)—C(24)—C(19) | 120.0 |
| C(23)—C(24)—H(24) | 120.0 |
| C(19)—C(24)—H(24) | 120.0 |
| O(7)—C(25)—N(5) | 118.6(14) |
| O(7)—C(25)—C(31) | 117.7(14) |
| N(5)—C(25)—C(31) | 123.7(14) |
| N(5)—C(26)—C(27) | 113.4(12) |
| N(5)—C(26)—B(3) | 100.1(12) |
| C(27)—C(26)—B(3) | 119.2(13) |
| N(5)—C(26)—H(26) | 107.8 |
| C(27)—C(26)—H(26) | 107.8 |
| B(3)—C(26)—H(26) | 107.8 |
| C(26)—C(27)—C(28) | 112.4(14) |
| C(26)—C(27)—H(27A) | 109.1 |
| C(28)—C(27)—H(27A) | 109.1 |
| C(26)—C(27)—H(27B) | 109.1 |
| C(28)—C(27)—H(27B) | 109.1 |
| H(27A)—C(27)—H(27B) | 107.8 |
| C(29)—C(28)—C(30) | 112.5(18) |
| C(29)—C(28)—C(27) | 111.8(16) |
| C(30)—C(28)—C(27) | 108.2(16) |
| C(29)—C(28)—H(28) | 108.1 |
| C(30)—C(28)—H(28) | 108.1 |
| C(27)—C(28)—H(28) | 108.1 |
| C(28)—C(29)—H(29A) | 109.5 |
| C(28)—C(29)—H(29B) | 109.5 |
| H(29A)—C(29)—H(29B) | 109.5 |
| C(28)—C(29)—H(29C) | 109.5 |
| H(29A)—C(29)—H(29C) | 109.5 |
| H(29B)—C(29)—H(29C) | 109.5 |
| C(28)—C(30)—H(30A) | 109.5 |
| C(28)—C(30)—H(30B) | 109.5 |
| H(30A)—C(30)—H(30B) | 109.5 |
| C(28)—C(30)—H(30C) | 109.5 |
| H(30A)—C(30)—H(30C) | 109.5 |
| H(30B)—C(30)—H(30C) | 109.5 |
| N(6)—C(31)—C(25) | 112.1(13) |
| N(6)—C(31)—H(31A) | 109.2 |
| C(25)—C(31)—H(31A) | 109.2 |
| N(6)—C(31)—H(31B) | 109.2 |
| C(25)—C(31)—H(31B) | 109.2 |
| H(31A)—C(31)—H(31B) | 107.9 |
| O(8)—C(32)—N(6) | 122.2(15) |
| O(8)—C(32)—C(33) | 120.3(15) |
| N(6)—C(32)—C(33) | 117.4(15) |
| C(38)—C(33)—C(34) | 119.3(16) |
| C(38)—C(33)—C(32) | 119.5(15) |
| C(34)—C(33)—C(32) | 121.1(15) |
| C(33)—C(34)—C(35) | 120.9(19) |
| C(33)—C(34)—Cl(4) | 120.7(15) |
| C(35)—C(34)—Cl(4) | 118.3(16) |
| C(36)—C(35)—C(34) | 117(2) |
| C(36)—C(35)—H(35) | 121.5 |
| C(34)—C(35)—H(35) | 121.5 |
| C(35)—C(36)—C(37) | 122(2) |
| C(35)—C(36)—H(36) | 119.2 |
| C(37)—C(36)—H(36) | 119.2 |
| C(38)—C(37)—C(36) | 118.3(18) |
| C(38)—C(37)—Cl(5) | 123.1(14) |
| C(36)—C(37)—Cl(5) | 118.6(15) |

TABLE 6-continued

Bond Angles in Degrees for Ixazomib Pattern F

| | |
|---|---|
| C(37)—C(38)—C(33) | 123.0(17) |
| C(37)—C(38)—H(38) | 118.5 |
| C(33)—C(38)—H(38) | 118.5 |
| C(2)—C(39)—C(40) | 118.2(16) |
| C(2)—C(39)—H(39) | 120.9 |
| C(40)—C(39)—H(39) | 120.9 |
| C(41)—C(40)—C(39) | 120.1(16) |
| C(41)—C(40)—Cl(6) | 122.7(15) |
| C(39)—C(40)—Cl(6) | 117.1(13) |
| C(40)—C(41)—C(42) | 119.3(18) |
| C(40)—C(41)—H(41) | 120.3 |
| C(42)—C(41)—H(41) | 120.3 |
| C(41)—C(42)—C(1) | 121.8(18) |
| C(41)—C(42)—H(42) | 119.1 |
| C(1)—C(42)—H(42) | 119.1 |
| C(44)—C(43)—C(84) | 118.8(16) |
| C(44)—C(43)—Cl(7) | 121.5(14) |
| C(84)—C(43)—Cl(7) | 119.6(14) |
| C(43)—C(44)—C(81) | 119.7(17) |
| C(43)—C(44)—C(45) | 122.7(15) |
| C(81)—C(44)—C(45) | 117.4(15) |
| O(10)—C(45)—N(7) | 122.4(16) |
| O(10)—C(45)—C(44) | 121.9(15) |
| N(7)—C(45)—C(44) | 115.8(15) |
| N(7)—C(46)—C(47) | 113.6(13) |
| N(7)—C(46)—H(46A) | 108.8 |
| C(47)—C(46)—H(46A) | 108.8 |
| N(7)—C(46)—H(46B) | 108.8 |
| C(47)—C(46)—H(46B) | 108.8 |
| H(46A)—C(46)—H(46B) | 107.7 |
| O(11)—C(47)—N(8) | 120.7(14) |
| O(11)—C(47)—C(46) | 121.8(15) |
| N(8)—C(47)—C(46) | 117.3(14) |
| N(8)—C(48)—C(49) | 111.0(12) |
| N(8)—C(48)—B(4) | 107.1(12) |
| C(49)—C(48)—B(4) | 106.9(12) |
| N(8)—C(48)—H(48) | 110.6 |
| C(49)—C(48)—H(48) | 110.6 |
| B(4)—C(48)—H(48) | 110.6 |
| C(50)—C(49)—C(48) | 115.4(13) |
| C(50)—C(49)—H(49A) | 108.4 |
| C(48)—C(49)—H(49A) | 108.4 |
| C(50)—C(49)—H(49B) | 108.4 |
| C(48)—C(49)—H(49B) | 108.4 |
| H(49A)—C(49)—H(49B) | 107.5 |
| C(52)—C(50)—C(51) | 111.8(14) |
| C(52)—C(50)—C(49) | 108.8(14) |
| C(51)—C(50)—C(49) | 114.9(13) |
| C(52)—C(50)—H(50) | 107.0 |
| C(51)—C(50)—H(50) | 107.0 |
| C(49)—C(50)—H(50) | 107.0 |
| C(50)—C(51)—H(51A) | 109.5 |
| C(50)—C(51)—H(51B) | 109.5 |
| H(51A)—C(51)—H(51B) | 109.5 |
| C(50)—C(51)—H(51C) | 109.5 |
| H(51A)—C(51)—H(51C) | 109.5 |
| H(51B)—C(51)—H(51C) | 109.5 |
| C(50)—C(52)—H(52A) | 109.5 |
| C(50)—C(52)—H(52B) | 109.5 |
| H(52A)—C(52)—H(52B) | 109.5 |
| C(50)—C(52)—H(52C) | 109.5 |
| H(52A)—C(52)—H(52C) | 109.5 |
| H(52B)—C(52)—H(52C) | 109.5 |
| O(13)—C(53)—N(9) | 119.9(14) |
| O(13)—C(53)—C(59) | 118.5(14) |
| N(9)—C(53)—C(59) | 121.5(14) |
| N(9)—C(54)—C(55) | 109.3(12) |
| N(9)—C(54)—B(5) | 103.5(12) |
| C(55)—C(54)—B(5) | 116.9(13) |
| N(9)—C(54)—H(54) | 108.9 |
| C(55)—C(54)—H(54) | 108.9 |
| B(5)—C(54)—H(54) | 108.9 |
| C(56)—C(55)—C(54) | 117.7(13) |
| C(56)—C(55)—H(55A) | 107.9 |
| C(54)—C(55)—H(55A) | 107.9 |
| C(56)—C(55)—H(55B) | 107.9 |
| C(54)—C(55)—H(55B) | 107.9 |
| H(55A)—C(55)—H(55B) | 107.2 |

TABLE 6-continued

Bond Angles in Degrees for Ixazomib Pattern F

| Atoms | Angle |
|---|---|
| C(58)—C(56)—C(55) | 113.3(15) |
| C(58)—C(56)—C(57) | 111.5(17) |
| C(55)—C(56)—C(57) | 109.4(15) |
| C(58)—C(56)—H(56) | 107.5 |
| C(55)—C(56)—H(56) | 107.5 |
| C(57)—C(56)—H(56) | 107.5 |
| C(56)—C(57)—H(57A) | 109.5 |
| C(56)—C(57)—H(57B) | 109.5 |
| H(57A)—C(57)—H(57B) | 109.5 |
| C(56)—C(57)—H(57C) | 109.5 |
| H(57A)—C(57)—H(57C) | 109.5 |
| H(57B)—C(57)—H(57C) | 109.5 |
| C(56)—C(58)—H(58A) | 109.5 |
| C(56)—C(58)—H(58B) | 109.5 |
| H(58A)—C(58)—H(58B) | 109.5 |
| C(56)—C(58)—H(58C) | 109.5 |
| H(58A)—C(58)—H(58C) | 109.5 |
| H(58B)—C(58)—H(58C) | 109.5 |
| N(10)—C(59)—C(53) | 112.3(13) |
| N(10)—C(59)—H(59A) | 109.1 |
| C(53)—C(59)—H(59A) | 109.1 |
| N(10)—C(59)—H(59B) | 109.1 |
| C(53)—C(59)—H(59B) | 109.1 |
| H(59A)—C(59)—H(59B) | 107.9 |
| O(14)—C(60)—N(10) | 123.9(15) |
| O(14)—C(60)—C(61) | 119.8(14) |
| N(10)—C(60)—C(61) | 116.3(14) |
| C(62)—C(61)—C(66) | 120.0 |
| C(62)—C(61)—C(60) | 123.2(10) |
| C(66)—C(61)—C(60) | 116.8(10) |
| C(61)—C(62)—C(63) | 120.0 |
| C(61)—C(62)—Cl(8) | 119.9(9) |
| C(63)—C(62)—Cl(8) | 120.1(9) |
| C(64)—C(63)—C(62) | 120.0 |
| C(64)—C(63)—H(63) | 120.0 |
| C(62)—C(63)—H(63) | 120.0 |
| C(63)—C(64)—C(65) | 120.0 |
| C(63)—C(64)—H(64) | 120.0 |
| C(65)—C(64)—H(64) | 120.0 |
| C(66)—C(65)—C(64) | 120.0 |
| C(66)—C(65)—Cl(9) | 119.8(9) |
| C(64)—C(65)—Cl(9) | 120.2(9) |
| C(65)—C(66)—C(61) | 120.0 |
| C(65)—C(66)—H(66) | 120.0 |
| C(61)—C(66)—H(66) | 120.0 |
| O(16)—C(67)—N(11) | 117.1(14) |
| O(16)—C(67)—C(73) | 119.0(14) |
| N(11)—C(67)—C(73) | 124.0(14) |
| N(11)—C(68)—C(69) | 112.6(12) |
| N(11)—C(68)—B(6) | 99.9(12) |
| C(69)—C(68)—B(6) | 118.3(13) |
| N(11)—C(68)—H(68) | 108.5 |
| C(69)—C(68)—H(68) | 108.5 |
| B(6)—C(68)—H(68) | 108.5 |
| C(68)—C(69)—C(70) | 113.2(14) |
| C(68)—C(69)—H(69A) | 108.9 |
| C(70)—C(69)—H(69A) | 108.9 |
| C(68)—C(69)—H(69B) | 108.9 |
| C(70)—C(69)—H(69B) | 108.9 |
| H(69A)—C(69)—H(69B) | 107.7 |
| C(71)—C(70)—C(72) | 112.9(17) |
| C(71)—C(70)—C(69) | 111.7(15) |
| C(72)—C(70)—C(69) | 107.3(15) |
| C(71)—C(70)—H(70) | 108.2 |
| C(72)—C(70)—H(70) | 108.2 |
| C(69)—C(70)—H(70) | 108.2 |
| C(70)—C(71)—H(71A) | 109.5 |
| C(70)—C(71)—H(71B) | 109.5 |
| H(71A)—C(71)—H(71B) | 109.5 |
| C(70)—C(71)—H(71C) | 109.5 |
| H(71A)—C(71)—H(71C) | 109.5 |
| H(71B)—C(71)—H(71C) | 109.5 |
| C(70)—C(72)—H(72A) | 109.5 |
| C(70)—C(72)—H(72B) | 109.5 |
| H(72A)—C(72)—H(72B) | 109.5 |
| C(70)—C(72)—H(72C) | 109.5 |
| H(72A)—C(72)—H(72C) | 109.5 |
| H(72B)—C(72)—H(72C) | 109.5 |
| N(12)—C(73)—C(67) | 111.9(13) |
| N(12)—C(73)—H(73A) | 109.2 |
| C(67)—C(73)—H(73A) | 109.2 |
| N(12)—C(73)—H(73B) | 109.2 |
| C(67)—C(73)—H(73B) | 109.2 |
| H(73A)—C(73)—H(73B) | 107.9 |
| O(17)—C(74)—N(12) | 122.9(16) |
| O(17)—C(74)—C(75) | 119.8(15) |
| N(12)—C(74)—C(75) | 117.3(15) |
| C(76)—C(75)—C(80) | 119.4(17) |
| C(76)—C(75)—C(74) | 123.2(17) |
| C(80)—C(75)—C(74) | 117.4(15) |
| C(75)—C(76)—C(77) | 121.3(19) |
| C(75)—C(76)—Cl(10) | 120.2(16) |
| C(77)—C(76)—Cl(10) | 118.5(16) |
| C(76)—C(77)—C(78) | 116.7(19) |
| C(76)—C(77)—H(77) | 121.6 |
| C(78)—C(77)—H(77) | 121.6 |
| C(79)—C(78)—C(77) | 122.9(19) |
| C(79)—C(78)—H(78) | 118.6 |
| C(77)—C(78)—H(78) | 118.6 |
| C(80)—C(79)—C(78) | 118.8(17) |
| C(80)—C(79)—Cl(11) | 121.0(14) |
| C(78)—C(79)—Cl(11) | 120.2(15) |
| C(79)—C(80)—C(75) | 120.7(16) |
| C(79)—C(80)—H(80) | 119.6 |
| C(75)—C(80)—H(80) | 119.6 |
| C(44)—C(81)—C(82) | 119.5(17) |
| C(44)—C(81)—H(81) | 120.2 |
| C(82)—C(81)—H(81) | 120.2 |
| C(83)—C(82)—C(81) | 120.1(17) |
| C(83)—C(82)—Cl(12) | 121.7(15) |
| C(81)—C(82)—Cl(12) | 118.1(14) |
| C(82)—C(83)—C(84) | 118.9(18) |
| C(82)—C(83)—H(83) | 120.6 |
| C(84)—C(83)—H(83) | 120.6 |
| C(83)—C(84)—C(43) | 122.6(18) |
| C(83)—C(84)—H(84) | 118.7 |
| C(43)—C(84)—H(84) | 118.7 |
| C(86)—C(85)—C(126) | 117.5(18) |
| C(86)—C(85)—Cl(13) | 121.1(15) |
| C(126)—C(85)—Cl(13) | 121.3(16) |
| C(85)—C(86)—C(123) | 121.8(18) |
| C(85)—C(86)—C(87) | 121.5(16) |
| C(123)—C(86)—C(87) | 116.7(16) |
| O(19)—C(87)—N(13) | 122.8(16) |
| O(19)—C(87)—C(86) | 120.7(15) |
| N(13)—C(87)—C(86) | 116.5(15) |
| N(13)—C(88)—C(89) | 113.4(13) |
| N(13)—C(88)—H(88A) | 108.9 |
| C(89)—C(88)—H(88A) | 108.9 |
| N(13)—C(88)—H(88B) | 108.9 |
| C(89)—C(88)—H(88B) | 108.9 |
| H(88A)—C(88)—H(88B) | 107.7 |
| O(20)—C(89)—N(14) | 121.9(15) |
| O(20)—C(89)—C(88) | 119.5(15) |
| N(14)—C(89)—C(88) | 118.6(15) |
| N(14)—C(90)—B(7) | 106.2(12) |
| N(14)—C(90)—C(91) | 109.0(12) |
| B(7)—C(90)—C(91) | 110.1(13) |
| N(14)—C(90)—H(90) | 110.5 |
| B(7)—C(90)—H(90) | 110.5 |
| C(91)—C(90)—H(90) | 110.5 |
| C(92)—C(91)—C(90) | 117.1(13) |
| C(92)—C(91)—H(91A) | 108.0 |
| C(90)—C(91)—H(91A) | 108.0 |
| C(92)—C(91)—H(91B) | 108.0 |
| C(90)—C(91)—H(91B) | 108.0 |
| H(91A)—C(91)—H(91B) | 107.3 |
| C(93)—C(92)—C(94) | 110.4(13) |
| C(93)—C(92)—C(91) | 113.6(13) |
| C(94)—C(92)—C(91) | 108.5(13) |
| C(93)—C(92)—H(92) | 108.0 |
| C(94)—C(92)—H(92) | 108.0 |
| C(91)—C(92)—H(92) | 108.0 |
| C(92)—C(93)—H(93A) | 109.5 |
| C(92)—C(93)—H(93B) | 109.5 |
| H(93A)—C(93)—H(93B) | 109.5 |

TABLE 6-continued

Bond Angles in Degrees for Ixazomib Pattern F

| Atoms | Angle |
|---|---|
| C(92)—C(93)—H(93C) | 109.5 |
| H(93A)—C(93)—H(93C) | 109.5 |
| H(93B)—C(93)—H(93C) | 109.5 |
| C(92)—C(94)—H(94A) | 109.5 |
| C(92)—C(94)—H(94B) | 109.5 |
| H(94A)—C(94)—H(94B) | 109.5 |
| C(92)—C(94)—H(94C) | 109.5 |
| H(94A)—C(94)—H(94C) | 109.5 |
| H(94B)—C(94)—H(94C) | 109.5 |
| O(22)—C(95)—N(15) | 117.4(14) |
| O(22)—C(95)—C(101) | 117.7(14) |
| N(15)—C(95)—C(101) | 124.9(14) |
| N(15)—C(96)—C(97) | 113.7(12) |
| N(15)—C(96)—B(8) | 99.8(12) |
| C(97)—C(96)—B(8) | 116.1(13) |
| N(15)—C(96)—H(96) | 108.9 |
| C(97)—C(96)—H(96) | 108.9 |
| B(8)—C(96)—H(96) | 108.9 |
| C(98)—C(100)—H(10D) | 109.5 |
| C(98)—C(100)—H(10E) | 109.5 |
| H(10D)—C(100)—H(10E) | 109.5 |
| C(98)—C(100)—H(10F) | 109.5 |
| H(10D)—C(100)—H(10F) | 109.5 |
| H(10E)—C(100)—H(10F) | 109.5 |
| N(16)—C(101)—C(95) | 114.4(12) |
| N(16)—C(101)—H(10G) | 108.7 |
| C(95)—C(101)—H(10G) | 108.7 |
| N(16)—C(101)—H(10H) | 108.7 |
| C(95)—C(101)—H(10H) | 108.7 |
| H(10G)—C(101)—H(10H) | 107.6 |
| O(23)—C(102)—N(16) | 120.7(15) |
| O(23)—C(102)—C(103) | 120.4(15) |
| N(16)—C(102)—C(103) | 118.9(15) |
| C(108)—C(103)—C(104) | 121.9(16) |
| C(108)—C(103)—C(102) | 117.7(15) |
| C(104)—C(103)—C(102) | 120.3(15) |
| C(105)—C(104)—C(103) | 117.1(16) |
| C(105)—C(104)—Cl(14) | 121.4(14) |
| C(103)—C(104)—Cl(14) | 121.5(14) |
| C(106)—C(105)—C(104) | 120.2(19) |
| C(106)—C(105)—H(105) | 119.9 |
| C(104)—C(105)—H(105) | 119.9 |
| C(105)—C(106)—C(107) | 120(2) |
| C(105)—C(106)—H(106) | 119.8 |
| C(107)—C(106)—H(106) | 119.8 |
| C(108)—C(107)—C(106) | 122.3(18) |
| C(108)—C(107)—Cl(15) | 119.0(14) |
| C(106)—C(107)—Cl(15) | 118.7(15) |
| C(107)—C(108)—C(103) | 118.0(16) |
| C(107)—C(108)—H(108) | 121.0 |
| C(103)—C(108)—H(108) | 121.0 |
| N(17)—C(109)—O(25) | 119.0(14) |
| N(17)—C(109)—C(115) | 122.6(14) |
| O(25)—C(109)—C(115) | 118.3(14) |
| N(17)—C(110)—C(111) | 110.1(11) |
| N(17)—C(110)—B(9) | 103.2(12) |
| C(111)—C(110)—B(9) | 116.5(12) |
| N(17)—C(110)—H(110) | 108.9 |
| C(111)—C(110)—H(110) | 108.9 |
| B(9)—C(110)—H(110) | 108.9 |
| C(112)—C(111)—C(110) | 117.5(13) |
| C(112)—C(111)—H(11A) | 107.9 |
| C(110)—C(111)—H(11A) | 107.9 |
| C(112)—C(111)—H(11B) | 107.9 |
| C(110)—C(111)—H(11B) | 107.9 |
| H(11A)—C(111)—H(11B) | 107.2 |
| C(114)—C(112)—C(111) | 113.4(14) |
| C(114)—C(112)—C(113) | 109.2(16) |
| C(111)—C(112)—C(113) | 110.3(14) |
| C(114)—C(112)—H(112) | 107.9 |
| C(111)—C(112)—H(112) | 107.9 |
| C(113)—C(112)—H(112) | 107.9 |
| C(112)—C(113)—H(11A) | 109.5 |
| C(112)—C(113)—H(11B) | 109.5 |
| H(11A)—C(113)—H(11B) | 109.5 |
| C(112)—C(113)—H(11C) | 109.5 |
| H(11A)—C(113)—H(11C) | 109.5 |
| H(11B)—C(113)—H(11C) | 109.5 |
| C(112)—C(114)—H(11D) | 109.5 |
| C(112)—C(114)—H(11E) | 109.5 |
| H(11D)—C(114)—H(11E) | 109.5 |
| C(112)—C(114)—H(11F) | 109.5 |
| H(11D)—C(114)—H(11F) | 109.5 |
| H(11E)—C(114)—H(11F) | 109.5 |
| N(18)—C(115)—C(109) | 113.1(12) |
| N(18)—C(115)—H(11G) | 109.0 |
| C(109)—C(115)—H(11G) | 109.0 |
| N(18)—C(115)—H(11H) | 109.0 |
| C(109)—C(115)—H(11H) | 109.0 |
| H(11G)—C(115)—H(11H) | 107.8 |
| O(26)—C(116)—N(18) | 125.1(15) |
| O(26)—C(116)—C(117) | 122.1(14) |
| N(18)—C(116)—C(117) | 112.6(13) |
| C(118)—C(117)—C(122) | 120.0 |
| C(118)—C(117)—C(116) | 119.6(10) |
| C(122)—C(117)—C(116) | 120.4(10) |
| C(119)—C(118)—C(117) | 120.0 |
| C(119)—C(118)—Cl(16) | 117.8(8) |
| C(117)—C(118)—Cl(16) | 121.9(8) |
| C(118)—C(119)—C(120) | 120.0 |
| C(118)—C(119)—H(119) | 120.0 |
| C(120)—C(119)—H(119) | 120.0 |
| C(121)—C(120)—C(119) | 120.0 |
| C(121)—C(120)—H(120) | 120.0 |
| C(119)—C(120)—H(120) | 120.0 |
| C(122)—C(121)—C(120) | 120.0 |
| C(122)—C(121)—Cl(17) | 117.3(8) |
| C(120)—C(121)—Cl(17) | 122.7(8) |
| C(121)—C(122)—C(117) | 120.0 |
| C(121)—C(122)—H(122) | 120.0 |
| C(117)—C(122)—H(122) | 120.0 |
| C(86)—C(123)—C(124) | 117.3(17) |
| C(86)—C(123)—H(123) | 121.4 |
| C(124)—C(123)—H(123) | 121.4 |
| C(125)—C(124)—C(123) | 122.7(18) |
| C(125)—C(124)—Cl(18) | 119.3(16) |
| C(123)—C(124)—Cl(18) | 118.0(14) |
| C(124)—C(125)—C(126) | 118(2) |
| C(124)—C(125)—H(125) | 120.9 |
| C(126)—C(125)—H(125) | 120.9 |
| C(125)—C(126)—C(85) | 122(2) |
| C(125)—C(126)—H(126) | 118.8 |
| C(85)—C(126)—H(126) | 118.8 |
| O(3)—B(1)—O(9) | 121.6(15) |
| O(3)—B(1)—C(6) | 117.7(14) |
| O(9)—B(1)—C(6) | 120.7(14) |
| O(6)—B(2)—O(3) | 112.8(12) |
| O(6)—B(2)—O(4) | 106.9(12) |
| O(3)—B(2)—O(4) | 103.9(11) |
| O(6)—B(2)—C(12) | 118.0(13) |
| O(3)—B(2)—C(12) | 113.1(13) |
| O(4)—B(2)—C(12) | 100.0(11) |
| O(6)—B(3)—O(9) | 114.0(12) |
| O(6)—B(3)—O(7) | 109.4(12) |
| O(9)—B(3)—O(7) | 104.1(12) |
| O(6)—B(3)—C(26) | 115.4(13) |
| O(9)—B(3)—C(26) | 113.8(12) |
| O(7)—B(3)—C(26) | 98.2(11) |
| O(12)—B(4)—O(18) | 124.5(15) |
| O(12)—B(4)—C(48) | 116.7(13) |
| O(18)—B(4)—C(48) | 118.8(13) |
| O(15)—B(5)—O(12) | 113.1(12) |
| O(15)—B(5)—C(54) | 118.8(13) |
| O(12)—B(5)—C(54) | 114.4(13) |
| O(15)—B(5)—O(13) | 105.3(12) |
| O(12)—B(5)—O(13) | 103.8(11) |
| C(54)—B(5)—O(13) | 98.6(11) |
| O(15)—B(6)—O(18) | 114.8(13) |
| O(15)—B(6)—O(16) | 108.5(12) |
| O(18)—B(6)—O(16) | 103.7(12) |
| O(15)—B(6)—C(68) | 114.6(13) |
| O(18)—B(6)—C(68) | 114.7(13) |
| O(16)—B(6)—C(68) | 98.3(11) |
| O(27)—B(7)—O(21) | 120.9(15) |
| O(27)—B(7)—C(90) | 118.7(14) |
| O(21)—B(7)—C(90) | 120.3(14) |

TABLE 6-continued

Bond Angles in Degrees for Ixazomib Pattern F

| | |
|---|---|
| O(24)—B(8)—O(21) | 115.8(13) |
| O(24)—B(8)—O(22) | 108.8(12) |
| O(21)—B(8)—O(22) | 101.6(12) |
| O(24)—B(8)—C(96) | 116.7(14) |
| O(21)—B(8)—C(96) | 113.2(13) |
| O(22)—B(8)—C(96) | 97.6(11) |
| O(24)—B(9)—O(27) | 113.9(12) |
| O(24)—B(9)—O(25) | 105.5(12) |
| O(27)—B(9)—O(25) | 105.5(11) |
| O(24)—B(9)—C(110) | 117.9(12) |
| O(27)—B(9)—C(110) | 113.1(13) |
| O(25)—B(9)—C(110) | 98.6(11) |
| C(98)—C(99)—H(99A) | 109.5 |
| C(98)—C(99)—H(99B) | 109.5 |
| H(99A)—C(99)—H(99B) | 109.5 |
| C(98)—C(99)—H(99C) | 109.5 |
| H(99A)—C(99)—H(99C) | 109.5 |
| H(99B)—C(99)—H(99C) | 109.5 |
| C(97)—C(98)—C(99) | 111.4(18) |
| C(97)—C(98)—C(100) | 109.1(17) |
| C(99)—C(98)—C(100) | 111(2) |
| C(97)—C(98)—H(98) | 108.4 |
| C(99)—C(98)—H(98) | 108.4 |
| C(100)—C(98)—H(98) | 108.4 |
| C(96)—C(97)—C(98) | 113.1(15) |
| C(96)—C(97)—H(97A) | 109.0 |
| C(98)—C(97)—H(97A) | 109.0 |
| C(96)—C(97)—H(97B) | 109.0 |
| C(98)—C(97)—H(97B) | 109.0 |
| H(97A)—C(97)—H(97B) | 107.8 |

Numbers in parentheses are estimated standard deviations in the least significant digits.

TABLE 7

Anisotropic Temperature Factor Coefficients - U's for Ixazomib Pattern F

| | $U^{11}$ | $U^{22}$ | $U^{33}$ | $U^{23}$ | $U^{13}$ | $U^{12}$ |
|---|---|---|---|---|---|---|
| Cl(1)  | 63(4)  | 29(3)  | 48(3) | 9(2)   | 24(3)  | −5(2) |
| Cl(2)  | 110(5) | 102(5) | 50(4) | 6(4)   | 31(4)  | 36(4) |
| Cl(3)  | 86(5)  | 66(4)  | 68(4) | 6(3)   | −17(4) | 16(4) |
| Cl(4)  | 58(4)  | 95(5)  | 52(4) | −8(3)  | 4(3)   | −39(3) |
| Cl(5)  | 36(3)  | 36(3)  | 62(3) | −2(2)  | 21(3)  | −17(2) |
| Cl(6)  | 86(4)  | 60(4)  | 28(3) | 5(2)   | 9(3)   | 17(3) |
| Cl(7)  | 95(4)  | 29(3)  | 45(3) | −6(2)  | 33(3)  | 8(3) |
| Cl(8)  | 197(9) | 94(5)  | 55(4) | −4(4)  | 44(5)  | −70(6) |
| Cl(9)  | 77(4)  | 71(4)  | 71(4) | −14(3) | −22(4) | −18(3) |
| Cl(10) | 73(4)  | 100(5) | 59(4) | −4(3)  | −11(3) | 64(4) |
| Cl(11) | 40(3)  | 35(3)  | 69(4) | 8(3)   | 25(3)  | 16(2) |
| Cl(12) | 90(4)  | 47(3)  | 26(3) | −2(2)  | 19(3)  | −7(3) |
| Cl(13) | 142(6) | 25(3)  | 89(5) | −15(3) | 78(5)  | −3(3) |
| Cl(14) | 74(4)  | 83(4)  | 53(4) | −4(3)  | −6(3)  | 49(4) |
| Cl(15) | 55(4)  | 44(3)  | 86(4) | 8(3)   | 40(3)  | 25(3) |
| Cl(16) | 93(5)  | 76(4)  | 50(4) | −5(3)  | 28(3)  | −19(4) |
| Cl(17) | 106(5) | 113(5) | 56(4) | 7(4)   | 42(4)  | −14(4) |
| Cl(18) | 82(4)  | 69(4)  | 26(3) | −7(3)  | 16(3)  | −7(3) |

The form of the anisotropic temperature factor is: $\exp[-2\pi^2 h^2 a^{*2} U(1,1) + k^2 b^{*2} U(2,2) + l^2 c^{*2} U(3,3) + 2hka^*b^*U(1,2) + 2hla^*c^*U(1,3) + 2klb^*c^*U(2,3)]$ where $a^*$, $b^*$, and $c^*$ are reciprocal lattice constants.

Example 10

The chemical stability assessment was performed on crystalline Pattern B using a 60/75 stress test (The International Conference on Harmonisation of Technical Requirements for Registration of Pharmaceuticals for Human Use, Stability Testing of New Drug Substances and Products, Q1A(R2), 2003). Samples were exposed to 60° C./75% relative humidity condition for 2 weeks and post-stress materials were analyzed by HPLC. Data at time-zero was also collected for all samples and served as references. The following table summarizes stability data obtained (peak area % measured by HPLC) for crystalline Pattern B.

| | % at t0 | % at 1 wk | % at 2 wk |
|---|---|---|---|
| Crystalline Pattern B | 99.3% | 94.2% | 79.5% |

Example 11

A suspension of non-crystalline solid of N,N',N"-[2,4,6-boroxintriyltris[[(1R)-3-methylbutylidene]imino(2-oxo-2,1-ethanediyl)]]tris(2,5-dichlorobenzamide) in a solvent or solvent mixture is agitated by stirring in a sealed vial at room temperature for a number of days. The resulting slurry is filtered to provide crystalline material. Following this general method, crystalline Pattern B was generated under the conditions described in the table below.

| Solvent System (vol:vol) | Conditions | Results |
|---|---|---|
| Acetone:Water (1:3) | Slurry at RT 2 d | crystalline Pattern B |
| DMF:Water (1:2) | Solution of non-crystalline solid in DMF prepared; water added to form precipitation; slurried at RT 3 d | crystalline Pattern B |
| isoPropyl acetate | Stir at RT 15 min (hazy solution); filter (clear solution); Partial Evaporation at RT 5 d | crystalline Pattern B |
| THF:Water (1:10) | Solution of non-crystalline solid in THF added to water at RT to form precipitation; Stir at RT 2 d | crystalline Pattern B |

Example 12

8.06 g of non-crystalline solid of N,N',N"-[2,4,6-boroxintriyltris[[(1R)-3-methylbutylidene]imino(2-oxo-2,1-ethanediyl)]]tris(2,5-dichlorobenzamide) was added to a 100 mL glass EasyMax™ reactor. 40 mL of ethyl acetate was added to the reactor. The sample was stirred at 250 rpm, blanketed by nitrogen, and the jacket was heated to 35° C. to obtain a clear solution. The jacket temperature was reduced to 10° C. Crystalline Pattern B resulting from EXAMPLE 7 was added to the reactor and a slurry was observed to form. The slurry was allowed to stir for 3 days and the solid was isolated and dried under nitrogen for 4 hours to provide crystalline Pattern B.

Example 13

To a suspension of non-crystalline solid of N,N',N"-[2,4,6-boroxintriyltris[[(1R)-3-methylbutylidene]imino(2-oxo-2,1-ethanediyl)]]tris(2,5-dichlorobenzamide) in a solvent mixture is added crystalline Pattern B resulting from EXAMPLE 12 at room temperature. The suspension is stirred at RT for 5 days. The resulting slurry was filtered to provide crystalline material. Following this general method, crystalline Pattern B was generated under the conditions described in the table below

| Solvent System (vol:vol) | Results |
|---|---|
| THF:ACN (1:5) | crystalline Pattern B |

-continued

| Solvent System (vol:vol) | Results |
|---|---|
| THF:diisopropyl ether (1:5) | crystalline Pattern B |
| THF:Toluene (1:5) | crystalline Pattern B |

We claim:

1. A crystalline form comprising N,N',N"-[2,4,6-boroxin-triyltris[[(1R)-3-methylbutylidene]imino(2-oxo-2,1-ethanediyl)]]tris(2,5-dichlorobenzamide) having the structure of Formula (1b):

Formula (Ib)

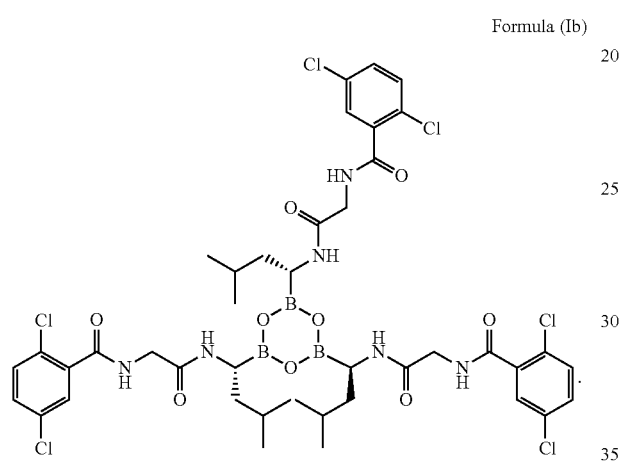

2. The crystalline form according to claim 1, wherein the crystalline form is crystalline Pattern B comprising an X-ray powder diffraction pattern having characteristic peaks expressed in degrees two-theta at approximately 5.79±0.20, 10.63±0.20, 16.06±0.20, and 23.58±0.20.

3. The crystalline form according to claim 1, wherein the crystalline form is crystalline Pattern B comprising an X-ray powder diffraction pattern having characteristic peaks expressed in degrees two-theta at approximately 5.79±0.20, 10.63±0.20, 16.06±0.20, 17.12±0.20, 17.93±0.20, 19.69±0.20, 23.58±0.20, 24.17±0.20 and 24.93±0.20.

4. The crystalline form according to claim 1, wherein the crystalline form is crystalline Pattern B comprising an X-ray powder diffraction pattern having a reference peak expressed in degrees two-theta at 5.79±0.20, and having peaks in degrees two-theta angles of 4.84, 10.27, 17.79 relative to the reference peak.

5. The crystalline form according to claim 1, wherein the crystalline form is crystalline Pattern B comprising an X-ray powder diffraction pattern having a reference peak expressed in degrees two-theta at 5.79±0.20, and having peaks in degrees two-theta angles of 4.84, 10.27, 11.33, 12.14, 13.90, 17.79, 18.38, 19.14 relative to the reference peak.

6. The crystalline form according to claim 1, wherein the crystalline form is crystalline Pattern B comprising an X-ray powder diffraction pattern having characteristic peaks expressed in degrees two-theta at approximately:

| Angles (°2θ) ± 0.20 | Intensity (%) |
|---|---|
| 5.79 | 100 |
| 6.98 | 18 |
| 9.46 | 13 |
| 9.89 | 33 |
| 10.63 | 70 |
| 11.40 | 16 |
| 12.41 | 13 |
| 13.96 | 32 |
| 14.13 | 29 |
| 14.38 | 16 |
| 16.06 | 75 |
| 16.73 | 27 |
| 17.12 | 68 |
| 17.53 | 23 |
| 17.93 | 61 |
| 18.58 | 28 |
| 19.26 | 20 |
| 19.69 | 68 |
| 20.05 | 25 |
| 20.65 | 18 |
| 21.37 | 24 |
| 21.99 | 33 |
| 22.59 | 11 |
| 23.58 | 80 |
| 24.17 | 67 |
| 24.33 | 32 |
| 24.93 | 39 |
| 25.26 | 15 |
| 26.11 | 12 |
| 26.54 | 13 |
| 26.92 | 11 |
| 28.12 | 11 |
| 28.46 | 11 |
| 29.36 | 11 |
| 29.59 | 10. |

7. The crystalline form according to claim 1, having a DSC profile characterized by an endothermic transition at about 123.4° C.

8. The crystalline form according to claim 1, having a DSC profile characterized by an endothermic transition at about 120° C. to about 125° C.

9. The crystalline form according to claim 8, having a DSC profile characterized by an endothermic transition of about 123.0° C.

10. The crystalline form according to claim 1, having a TGA profile losing about 1.9% weight up to 150° C. at a temperature rate of 10° C. per minute, and decomposition at about 272±5° C.

11. The crystalline form according to claim 1, wherein the crystalline form is a monohydrate.

12. A method for the preparation of the crystalline form according to claim 1, wherein the crystalline form is crystalline Pattern B, comprising:

(a) adding a non-crystalline solid comprising a compound of Formula (Ib) to a solvent or solvent mixture Formula (Ib)

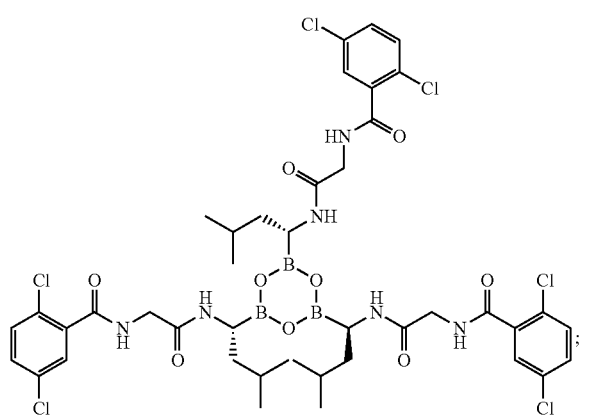

(b) stirring the resulting mixture for a sufficient amount of time to form crystalline Pattern B; and optionally
(c) isolating crystalline Pattern B.

13. The method according to claim 12, wherein the solvent or solvent mixture is acetone/water (1:3), DMF/water (1:2), iso-propyl acetate, or THF/water (1:10).

14. A method for the preparation of the crystalline form according to claim 1, wherein the crystalline form is crystalline Pattern B, comprising:
(a) dissolving or suspending a non-crystalline solid comprising a compound of Formula (Ib) in a solvent Formula (Ib)

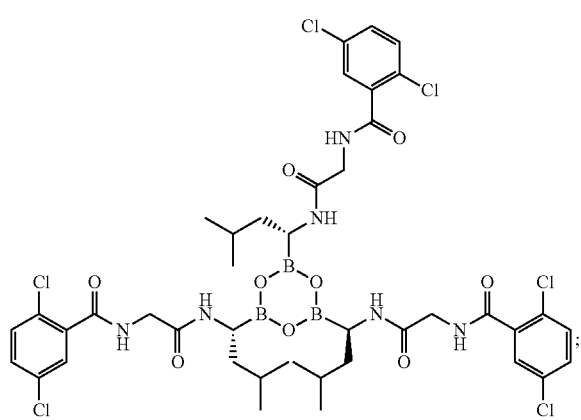

(b) adding a second agent to the suspension or solution at a predetermined temperature;

(c) stirring the above mixture for a sufficient amount of time to form crystalline Pattern B; and optionally
(d) isolating the resulting crystalline Pattern B.

15. The method according to claim 14, wherein the solvent is ethyl acetate.

16. The method according to claim 14, wherein the second agent is anethole, methyl benzoate, methyl cinnamate, triacetin, triethyl citrate, or caffeine.

17. The method of according claim 14, wherein the temperature is between about 15° C. to about 35° C.

18. A process for producing the crystalline form according to claim 1, wherein the crystalline form is crystalline Pattern B, comprising:
(a) adding crystalline Pattern B as seeding material to a solution of non-crystalline solid comprising the compound of Formula (Ib)

Formula (Ib)

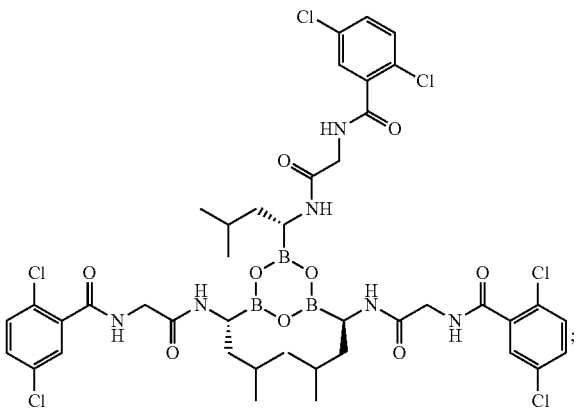

(b) stirring the solution at a predetermined temperature for a sufficient amount of time; and optionally
(c) collecting the resulting crystalline Pattern B.

19. The process according to claim 18, wherein the seeding material is about 0.1% to about 5%, or about 5% to about 10%, or about 10% to about 20% by weight of the amount of non-crystalline solid of Formula (Ib).

20. The process of claim 18, wherein the solution is ethyl acetate solution.

21. The process of claim 18, wherein the temperature is between about 15° C. to about 40° C.

22. The process of claim 18, wherein the amount of time is from 4 hours to 24 hours.

23. A pharmaceutical composition comprising the crystalline form of claim 1; and a pharmaceutically acceptable carrier.

* * * * *